(12) United States Patent
Kim et al.

(10) Patent No.: US 10,544,438 B2
(45) Date of Patent: Jan. 28, 2020

(54) COMPOSITION FOR PREPARING TAGATOSE AND METHOD FOR PREPARING TAGATOSE FROM FRUCTOSE

(71) Applicant: CJ CHEILJEDANG CORPORATION, Seoul (KR)

(72) Inventors: Yang Hee Kim, Suwon-si (KR); Sung Jae Yang, Suwon-si (KR); Young Mi Lee, Suwon-si (KR); Il Hyang Park, Suwon-si (KR); Seong Bo Kim, Seongnam-si (KR); Hyun Kug Cho, Seoul (KR); Seung Won Park, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 213 days.

(21) Appl. No.: 15/521,243

(22) PCT Filed: Oct. 19, 2015

(86) PCT No.: PCT/KR2015/011007
§ 371 (c)(1),
(2) Date: Apr. 21, 2017

(87) PCT Pub. No.: WO2016/064146
PCT Pub. Date: Apr. 28, 2016

(65) Prior Publication Data
US 2017/0306370 A1    Oct. 26, 2017

(30) Foreign Application Priority Data

Oct. 22, 2014  (KR) .................. 10-2014-0143703

(51) Int. Cl.
*C12P 19/02* (2006.01)
*C12P 19/24* (2006.01)

(52) U.S. Cl.
CPC .............. *C12P 19/02* (2013.01); *C12P 19/24* (2013.01); *C12Y 501/03* (2013.01)

(58) Field of Classification Search
None
See application file for complete search history.

(56) References Cited

FOREIGN PATENT DOCUMENTS

| KR | 10-2004-0035683 A | 4/2004 |
|----|-------------------|--------|
| KR | 10-2008-0053708 A | 6/2008 |
| KR | 10-2009-0082774 A | 7/2009 |
| RU | 2010131456 A      | 3/2009 |
| WO | 2014/196811 A1    | 12/2014 |
| WO | 2015/076563 A1    | 5/2015 |

OTHER PUBLICATIONS

International Search Report dated Feb. 24, 2016 of PCT/KR2015/011007 which is the parent application and its English translation—6 pages.

Office Action of corresponding Japanese Patent Application No. 2017-521088—4 pages (dated Dec. 3, 2018).
Rangarajan et al., "Mechanism of D-fructose isomerization by Arthrobacter D-xylose isomerase", Biochem. J., vol. 283—11 pages (1992).
Kim et al., "Novel Activity of UDP-Galactose-4-Epimerase for Free Monosaccharide and Activity Improvement by Active Site-Saturation Mutagenesis", Applied Biochemistry and Biotechnology, vol. 163, No. 3—10 pages (2011).
NCBI Reference Sequence, WP_012844026.1—1 page, (May 18, 2013).
NCBI Reference Sequence, WP_011943119.1—1 page, (May 16, 2013).
NCBI Reference Sequence, WP_012002872.1—1 page, (May 16, 2013).
NCBI Reference Sequence, WP_013150657.1—1 page, (May 18, 2013).
NCBI Reference Sequence, WP_012582608.1—1 page, (May 17, 2013).
NCBI Reference Sequence, WP_013788787.1—1 page, (May 18, 2013).
NCBI Reference Sequence, WP_006569468.1—1 page, (May 28, 2013).
Wanarska et al., "A method for the production of D-tagatose using a recombinant Pichia pastoris strain secreting B-D-galactosidase from *Arthrobacter chlorophenolicus* and a recombinant L-arabinose isomerase from *Arthrobacter* sp. 22c", Microbial Cell Factories, vol. 11, No. 113—15 pages, (2012).
Office Action of corresponding Russian Patent Application No. 2017113926/10(024365)—6 pages, (dated Mar. 7, 2018).
Extended European Search Report of corresponding European Patent Application No. 15852026.2—6 pages, (dated Mar. 12, 2018).
Office Action of corresponding Japanese Patent Application No. 2017-521088—5 pages, (dated Mar. 26, 2018).
GenBank Accession No. YP_002352137.1—2 pages, (May 16, 2014).
GenBank Accession No. ABQ46504.1—1 page, (Jan. 28, 2014).
GenBank Accession No. ABV33391.1—1 page, (Jan. 28, 2014).
GenBank Accession No. ACY48415.1—2 pages, (Dec. 11, 2013).
GenBank Accession No. ADH61429.1—1 page, (Jan. 28, 2014).
GenBank Accession No. AEF18057.1—1 page, (Dec. 31, 2013).
Beerens et al., "Enzymes for the biocatalytic production of rare sugars", J. Ind. Microbiol. Biotechnol., vol. 39—12 pages, (Feb. 14, 2012).

(Continued)

*Primary Examiner* — Kagnew H Gebreyesus
(74) *Attorney, Agent, or Firm* — Knobbe Martens Olson & Bear LLP

(57) ABSTRACT

The present invention relates to a composition for preparing tagatose, wherein the composition is used for preparing tagatose from fructose and contains a protein including any one amino acid sequence of SEQ ID NOS: 1 to 7 or a microorganism expressing the protein. In addition, the present invention relates to a method for preparing tagatose from fructose, the method comprising a step of allowing the composition to react with fructose.

20 Claims, 21 Drawing Sheets
Specification includes a Sequence Listing.

(56) References Cited

OTHER PUBLICATIONS

Oh, "Tagatose: properties, applications, and biotechnological processes", Appl. Microbiol. Biotechnol., vol. 76—8 pages, (May 10, 2007).
Kim, "Current studies on biological tagatose production using L-arabinose isomerase: a review and future perspective", Applied Microbiology and Biotechnology, vol. 65—7 pages, (Jul. 10, 2004).
Li et al., "Biosynthesis of rare hexoses using microorganisms and related enzymes", Beilstein Journal of Organic Chemistry, vol. 9—12 pages, (Nov. 12, 2013).
Rodionova et al., "Tagaturonate-fructuronate epimerase UxaE, a novel enzyme in the hexuronate catabolic network in Thermotoga maritima", Environmental Microbiology, vol. 14, No. 11—15 pages, (2012).

RM

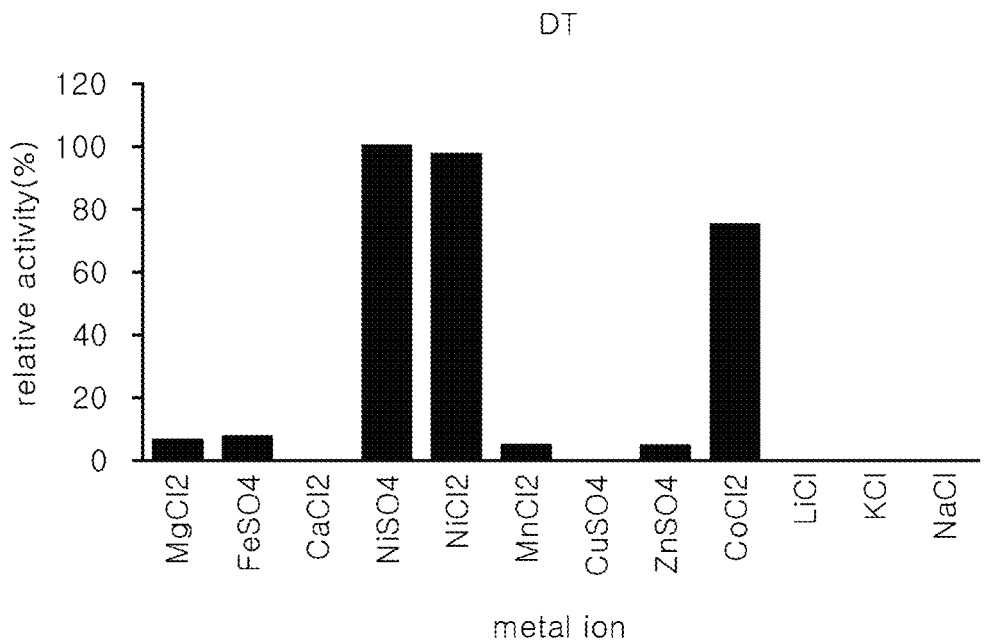

Fig. 5g

Fig. 6a: A amino acid sequence of protein derived from *Rhodothermus marinus*

MVTVLQTLLQRPRPLAEIDRAALARFLTDLIRQQVYPASL
EPTSEGVFFLARDGREKRLGILSEAGLHDFEGARHQLSLD
GRTLIFQSCPLTAANARALRQHLAWTAPRPLGLRASVGC
GDRLGLATPGHVRAVRKHKLAPVFAQQSIREMTRTGRTP
QQVLDEAMWGVFQEGWRQGYGADADHLKTEEDADRCI
EAGFTFFTIDPSAYVDNEVDTADAATLEAKVAALPWDAL
ETTLADLRRAYLGQHFQVGPYELSFEERTLLQALAKYGGA
IAHTARVYRHIAGRMGNRPFELEMSVDETEVPTSPAEHF
FVARELQRLGVRWISLAPRFVGRLEKGVDYIGDLEEFEAH
LKLHVAIARTLGPYKLSLHSGSDKFALYPLFARHAGELFH
LKTAGTSYLEALRAVAELDPPLFREILDFARDRYETDRATY
HVSALLERVPKASDVPDDALPALLEQFDTRQVLHVTFGS
VLTATDADGRPRFRDRLLAVLQENEETYYRLLEAHFDRHL
APFDAK

Fig. 6b: A amino acid sequence of protein derived from *Thermotoga petrophila*

MVLKVFKDHFGRGYEVYEKSYREKDSLSFFLTKGEEGKIL
VVAGEKAPEGLSFFKKQRVEGVSFFFCERNHENLEVLRKY
FPDLKPVRAGLRASFGTGDRLGITTPAHVRALKDSGLFPI
FAQQSVRENERTGRTWRDVLDDATWGVFQEGYSEGFGA
DADHVKRPEDLVSAAREGFTMFTIDPSDHVRNLSKLTEK
ERNEKFEEILRKERIDRIYLGKKYSVLGEKIEFDEKNLRDA
ALVYYDAIAHVDMMYQILKDETPDFDFEVSVDETETPTS
PLFHIFVVEELRRRGVEFTNLALRFIGEWEKGIDYKGDLA
QFEREIKMHAEIARMFEGYKISLHSGSDKFSVYPAFASAT
GGLFHVKTAGTSYLEAVKVISMVNPELFREIYRCALDHFE
EDRKSYHISADLSKVPEVEKVKDEDLPGLFEDINVRQLIH
VTYGSVLKDASLKERLFKTLEQNEELFYETVAKHIKRHVD
LLKG

Fig. 6c: A amino acid sequence of protein derived from *Thermotoga lettingae*

MAENIVEKFEKLFKGKYKIYYSSIRKLEKSFFFMIRDQKQK
YLISIAKKRICEKFEGKKIGRINDLDILMCPTNDYNCKVIR
TLFNINPSVCKKNTSFGFGDRLGLATPAHTTLINKYDVFP
VLAQQSVRELSRTHRNFKDVLDSAIWGIFESGYEGEFGA
DADHVKDINDLMQAAYEGYSMYTVDPSDHVKNIDKINQ
GELVEFYKSHPLRKEIEMIYSGKVFSFEKSKFTMEDKELFR
IFVTYVDAIEHVVKCYEAIKNTKKNFDFEVSIDETSIPTSP
LAHIFIVHELRRRGVDFQTLALRFVGQWQKAIDYIGDLSV
LESELSMHCEIVKSLSGYRLSLHSGSDKFSVYRIFTHYCD
GKLHVKTAGTSYLEAIRTVAEASPSLYRNIHKYALTCFEK
DNTSYHVTADINKIPDVDNVEDSKVVNLLDIPEVRQLIHI
TYGSVLTEKINGKYLFRDEIYRILHENEFLHYKRIRDHLGK
HLELLKN

Fig. 6d: A amino acid sequence of protein derived from *Thermoanaerobacter mathranii*

MVEKSILEKLTDFLLNHSFVLYPNSLRKLKEDTYIFVAKKD
ADKKIGILTKENFKLTSPYFVEDKNVKEIDFYLNLYPLSFE
NYLILKNFGISPTPCRQKSSFGTGDRLGLVTPAHIVALKE
YPVFPVLAQQSPRELEKTHRDFKDALLKVILGVLEAGYTG
EFGADADHIKDEKYLLRAIEAGYTMYTLDVSELLTKILDIS
SNQVMQISPQSKEIIEAFKGKKISISEEEYTIREDELYKSAL
IYEKAMNFVEKVYSILKEKVKDFDLEISIDEGEKDTTVEDH
IFVAEYLHKKGIDFWSLAPKFPGEFQKAIDYKGDINKFAV
ELKKHYAISQQLGGYKLSLHSGSDKFSIYEIFSEVTQHSFH
IKTSGTSWLQAVNLIFEKNKKLFYELYKIALNNLEESKKAY
KVLIDKDDFAEEPNLENVQILSQPEIKQLFHISYGVLLDEK
KEEIYDVLDKYEEEHYQFVSANIKNHLGKIFNN

Fig. 6e: A amino acid sequence of protein derived from *Dictyoglomus turgidum*

MLKLLNESLKPLSIFIYSESLRKINDDLYIFVAKIKDLKKIG
IVKQNQILYFSSPYFSEDKKIEGTNFLVNLYPLNFENYQKL
KEIIPISPKVCDKKISFGTGDRLGLITSAQLSALKEYDLFPI
LAQQSPRELIKTKRDFKDVLLKSAMGVLETGYTGKYGAD
ADHIKDEKYLMEAIDAGYTM YTLDISDFIEKIKDLSEKAL
KEKYEKVSSFSKKIIDKYAGKRVKISDEEYFELSYNELCKS
AIVYEKALSFVEMVYEILKSKLSEFDIEVSIDEGERDTTPE
DHFFVAQFLHDKGIDFKSLAPKFPGEFQKGIDYIGDIKEF
ERALKKHYALTKALEGYRLSLHSGSDKFSIYKIFYKITEGN
FHIKTSGTSWLEAVKVIAKFFPDLFVELYQIALENLEESKK
AYKVNITKEEFPKEIKEDYMEFLHKDNVRQLFHISYGVLL
DEKRKEIYDLLNQKEKEHYQYVSENIKKHLKNLFEEE

Fig. 6f: A amino acid sequence of protein derived from *Thermoanaerobacterium xylanolyticum*

MVGNVSSVLKESGFQIYPDSLRKLGENTYIFVVKKQKEK
MIGILSNDELKLKEPYFSENKKISDNLQFNVYSFTFDNYV
TLNGRFHIGPTICRENASFGTGDRLGLATAAQLDALKKFN
VFPILAQQSPRELVKTNRDFKDVLLKVVLGVLETGYIGHY
GADADHIKDEKYLLEGIDAGYTMYTLDLSEQLFDVSGAT
SLEIKEKAKTLSDVSRKIVEDFSGKSLNVGFGGHLVSEDEL
LKSAVAYEAAMKFVEKVNDILKEKLNDFDLEISIDEGGKV
TTLEDHLFVAEYLHRNGIDFFSIAPKFPGEFEKAIDYVGD
VNEFERELKKHYDLTKLIGGYKLSLHSGSDKFSIYKIFSQT
TEKNFHIKTSGTSWLQAVNLIYKSDKEFYRELYKIALSNLE
ESKKSYKVLIKKDDFKDEPELDNSEFIIRPEIKQLFHISFGV
LLDLKGKEIKDMLYDYEEEHYKMVSDNIENHLKEIFYEK

Fig. 6g: A amino acid sequence of protein derived from *Thermoanaerobacter siderophilus*

MKEELSDYLLKNSFLLYPDSFRRLREDVYIFVAKKDSDKKI
GLLTNGNFKLSSPHFAEDKYVEELGFYINLYPLTYENYLIL
KDNFGISPVTCKEKASFGTGDRLGLATPAHIKALKNYNVF
PVLAQQSPRELVKTHRDFKDVFLKVILGVLEAGYAGGYG
ADADHIKDEKYLIEAIDAGYTMYTLDLSDLLVKISDMPKS
QLKEKAQSLSSQSREIIDRFKGKKFSISTDEDFAVSEDELY
KSALTYEKAMKFVEKVYGILKDRLQHFDLEISIDEGEKDT
TVEDHIFVAEYLHRKGIDFWSLAPKFPGEFQKAIDYKGDI
KKFTSGLKKHYFLSKKLGGYKLSLHSGSDKFSIYKIFNEIT
EGNFHIKTSGTSWLQAINIIFERDKDLFNDLYKIALDNLEE
SKKAYKVLIDRDDFPQTIQTEDSQILLKPEIKQLFHISYGV
LLDERRKEIYEVLNKYEEEHYEFVSKNIENHLKEIFNI

SEQUENCE LISTING

```
<160> NUMBER OF SEQ ID NOS: 7

<210> SEQ ID NO 1
<211> LENGTH: 519
<212> TYPE: PRT
<213> ORGANISM: Rhodothermus marinus

<400> SEQUENCE: 1

Met Val Thr Val Leu Gln Thr Leu Leu Gln Arg Pro Arg Pro Leu Ala
1               5                   10                  15

Glu Ile Asp Arg Ala Ala Leu Ala Arg Phe Leu Thr Asp Leu Ile Arg
            20                  25                  30

Gln Gln Val Tyr Pro Ala Ser Leu Glu Pro Thr Ser Glu Gly Val Phe
        35                  40                  45

Phe Leu Ala Arg Asp Gly Arg Glu Lys Arg Leu Gly Ile Leu Ser Glu
    50                  55                  60

Ala Gly Leu His Asp Phe Glu Gly Ala Arg His Gln Leu Ser Leu Asp
```

-continued

```
                65                  70                  75                  80
        Gly Arg Thr Leu Ile Phe Gln Ser Cys Pro Leu Thr Ala Ala Asn Ala
                            85                  90                  95
        Arg Ala Leu Arg Gln His Leu Ala Trp Thr Ala Pro Arg Pro Leu Gly
                            100                 105                 110
        Leu Arg Ala Ser Val Gly Cys Gly Asp Arg Leu Gly Leu Ala Thr Pro
                            115                 120                 125
        Gly His Val Arg Ala Val Arg Lys His Lys Leu Ala Pro Val Phe Ala
                            130                 135                 140
        Gln Gln Ser Ile Arg Glu Met Thr Arg Thr Gly Arg Thr Pro Gln Gln
        145                 150                 155                 160
        Val Leu Asp Glu Ala Met Trp Gly Val Phe Gln Gly Trp Arg Gln
                            165                 170                 175
        Gly Tyr Gly Ala Asp Ala Asp His Leu Lys Thr Glu Glu Asp Ala Asp
                            180                 185                 190
        Arg Cys Ile Glu Ala Gly Phe Thr Phe Phe Thr Ile Asp Pro Ser Ala
                            195                 200                 205
        Tyr Val Asp Asn Glu Val Asp Thr Ala Asp Ala Ala Thr Leu Glu Ala
                            210                 215                 220
        Lys Val Ala Ala Leu Pro Trp Asp Ala Leu Glu Thr Thr Leu Ala Asp
        225                 230                 235                 240
        Leu Arg Arg Ala Tyr Leu Gly Gln His Phe Gln Val Gly Pro Tyr Glu
                            245                 250                 255
        Leu Ser Phe Glu Glu Arg Thr Leu Leu Gln Ala Leu Ala Lys Tyr Gly
                            260                 265                 270
        Gly Ala Ile Ala His Thr Ala Arg Val Tyr Arg His Ile Ala Gly Arg
                            275                 280                 285
        Met Gly Asn Arg Pro Phe Glu Leu Glu Met Ser Val Asp Glu Thr Glu
                            290                 295                 300
        Val Pro Thr Ser Pro Ala Glu His Phe Phe Val Ala Arg Glu Leu Gln
        305                 310                 315                 320
        Arg Leu Gly Val Arg Trp Ile Ser Leu Ala Pro Arg Phe Val Gly Arg
                            325                 330                 335
        Leu Glu Lys Gly Val Asp Tyr Ile Gly Asp Leu Glu Glu Phe Glu Ala
                            340                 345                 350
        His Leu Lys Leu His Val Ala Ile Ala Arg Thr Leu Gly Pro Tyr Lys
                            355                 360                 365
        Leu Ser Leu His Ser Gly Ser Asp Lys Phe Ala Leu Tyr Pro Leu Phe
                            370                 375                 380
        Ala Arg His Ala Gly Glu Leu Phe His Leu Lys Thr Ala Gly Thr Ser
        385                 390                 395                 400
        Tyr Leu Glu Ala Leu Arg Ala Val Ala Glu Leu Asp Pro Pro Leu Phe
                            405                 410                 415
        Arg Glu Ile Leu Asp Phe Ala Arg Asp Arg Tyr Glu Thr Asp Arg Ala
                            420                 425                 430
        Thr Tyr His Val Ser Ala Leu Leu Glu Arg Val Pro Lys Ala Ser Asp
                            435                 440                 445
        Val Pro Asp Asp Ala Leu Pro Ala Leu Leu Glu Gln Phe Asp Thr Arg
                            450                 455                 460
        Gln Val Leu His Val Thr Phe Gly Ser Val Leu Thr Ala Thr Asp Ala
        465                 470                 475                 480
        Asp Gly Arg Pro Arg Phe Arg Asp Arg Leu Leu Ala Val Leu Gln Glu
                            485                 490                 495
```

```
Asn Glu Glu Thr Tyr Tyr Arg Leu Leu Glu Ala His Phe Asp Arg His
                500                 505                 510

Leu Ala Pro Phe Asp Ala Lys
        515

<210> SEQ ID NO 2
<211> LENGTH: 481
<212> TYPE: PRT
<213> ORGANISM: Thermotoga petrophila

<400> SEQUENCE: 2

Met Val Leu Lys Val Phe Lys Asp His Phe Gly Arg Gly Tyr Glu Val
1               5                   10                  15

Tyr Glu Lys Ser Tyr Arg Glu Lys Asp Ser Leu Ser Phe Phe Leu Thr
                20                  25                  30

Lys Gly Glu Glu Gly Lys Ile Leu Val Val Ala Gly Glu Lys Ala Pro
            35                  40                  45

Glu Gly Leu Ser Phe Phe Lys Lys Gln Arg Val Glu Gly Val Ser Phe
        50                  55                  60

Phe Phe Cys Glu Arg Asn His Glu Asn Leu Glu Val Leu Arg Lys Tyr
65                  70                  75                  80

Phe Pro Asp Leu Lys Pro Val Arg Ala Gly Leu Arg Ala Ser Phe Gly
                85                  90                  95

Thr Gly Asp Arg Leu Gly Ile Thr Thr Pro Ala His Val Arg Ala Leu
            100                 105                 110

Lys Asp Ser Gly Leu Phe Pro Ile Phe Ala Gln Gln Ser Val Arg Glu
        115                 120                 125

Asn Glu Arg Thr Gly Arg Thr Trp Arg Asp Val Leu Asp Asp Ala Thr
    130                 135                 140

Trp Gly Val Phe Gln Glu Gly Tyr Ser Glu Gly Phe Gly Ala Asp Ala
145                 150                 155                 160

Asp His Val Lys Arg Pro Glu Asp Leu Val Ser Ala Ala Arg Glu Gly
                165                 170                 175

Phe Thr Met Phe Thr Ile Asp Pro Ser Asp His Val Arg Asn Leu Ser
            180                 185                 190

Lys Leu Thr Glu Lys Glu Arg Asn Glu Lys Phe Glu Glu Ile Leu Arg
        195                 200                 205

Lys Glu Arg Ile Asp Arg Ile Tyr Leu Gly Lys Lys Tyr Ser Val Leu
    210                 215                 220

Gly Glu Lys Ile Glu Phe Asp Glu Lys Asn Leu Arg Asp Ala Ala Leu
225                 230                 235                 240

Val Tyr Tyr Asp Ala Ile Ala His Val Asp Met Met Tyr Gln Ile Leu
                245                 250                 255

Lys Asp Glu Thr Pro Asp Phe Asp Phe Glu Val Ser Val Asp Glu Thr
            260                 265                 270

Glu Thr Pro Thr Ser Pro Leu Phe His Ile Phe Val Val Glu Glu Leu
        275                 280                 285

Arg Arg Arg Gly Val Glu Phe Thr Asn Leu Ala Leu Arg Phe Ile Gly
    290                 295                 300

Glu Trp Glu Lys Gly Ile Asp Tyr Lys Gly Asp Leu Ala Gln Phe Glu
305                 310                 315                 320

Arg Glu Ile Lys Met His Ala Glu Ile Ala Arg Met Phe Glu Gly Tyr
                325                 330                 335

Lys Ile Ser Leu His Ser Gly Ser Asp Lys Phe Ser Val Tyr Pro Ala
```

-continued

```
                340             345             350
    Phe Ala Ser Ala Thr Gly Gly Leu Phe His Val Lys Thr Ala Gly Thr
                355                 360                 365

Ser Tyr Leu Glu Ala Val Lys Val Ile Ser Met Val Asn Pro Glu Leu
        370                 375                 380

Phe Arg Glu Ile Tyr Arg Cys Ala Leu Asp His Phe Glu Glu Asp Arg
    385                 390                 395                 400

Lys Ser Tyr His Ile Ser Ala Asp Leu Ser Lys Val Pro Glu Val Glu
                    405                 410                 415

Lys Val Lys Asp Glu Asp Leu Pro Gly Leu Phe Glu Asp Ile Asn Val
                420                 425                 430

Arg Gln Leu Ile His Val Thr Tyr Gly Ser Val Leu Lys Asp Ala Ser
                    435                 440                 445

Leu Lys Glu Arg Leu Phe Lys Thr Leu Glu Gln Asn Glu Glu Leu Phe
                450                 455                 460

Tyr Glu Thr Val Ala Lys His Ile Lys Arg His Val Asp Leu Leu Lys
    465                 470                 475                 480

Gly

<210> SEQ ID NO 3
<211> LENGTH: 489
<212> TYPE: PRT
<213> ORGANISM: Thermotoga lettingae

<400> SEQUENCE: 3

Met Ala Glu Asn Ile Val Glu Lys Phe Glu Lys Leu Phe Lys Gly Lys
    1               5                   10                  15

Tyr Lys Ile Tyr Tyr Ser Ser Ile Arg Lys Leu Glu Lys Ser Phe Phe
                    20                  25                  30

Phe Met Ile Arg Asp Gln Lys Gln Lys Tyr Leu Ile Ser Ile Ala Lys
                35                  40                  45

Lys Arg Ile Cys Glu Lys Phe Glu Gly Lys Lys Ile Gly Arg Ile Asn
    50                  55                  60

Asp Leu Asp Ile Leu Met Cys Pro Thr Asn Asp Tyr Asn Cys Lys Val
    65                  70                  75                  80

Ile Arg Thr Leu Phe Asn Ile Asn Pro Ser Val Cys Lys Lys Asn Thr
                    85                  90                  95

Ser Phe Gly Phe Gly Asp Arg Leu Gly Leu Ala Thr Pro Ala His Thr
                    100                 105                 110

Thr Leu Ile Asn Lys Tyr Asp Val Phe Pro Val Leu Ala Gln Gln Ser
                115                 120                 125

Val Arg Glu Leu Ser Arg Thr His Arg Asn Phe Lys Asp Val Leu Asp
    130                 135                 140

Ser Ala Ile Trp Gly Ile Phe Glu Ser Gly Tyr Glu Gly Glu Phe Gly
    145                 150                 155                 160

Ala Asp Ala Asp His Val Lys Ser Ile Asn Asp Leu Met Gln Ala Ala
                    165                 170                 175

Tyr Glu Gly Tyr Ser Met Tyr Thr Val Asp Pro Ser Asp His Val Lys
                    180                 185                 190

Asn Ile Asp Lys Ile Asn Gln Gly Glu Leu Val Glu Phe Tyr Lys Ser
                195                 200                 205

His Pro Leu Arg Lys Glu Ile Glu Met Ile Tyr Ser Gly Lys Val Phe
        210                 215                 220

Ser Phe Glu Lys Ser Lys Phe Thr Met Glu Asp Lys Glu Leu Phe Arg
```

```
            225                 230                 235                 240
        Ile Phe Val Thr Tyr Val Asp Ala Ile Glu His Val Val Lys Cys Tyr
                        245                 250                 255

Glu Ala Ile Lys Asn Thr Lys Lys Asn Phe Asp Phe Glu Val Ser Ile
                        260                 265                 270

Asp Glu Thr Ser Ile Pro Thr Ser Pro Leu Ala His Ile Phe Ile Val
                        275                 280                 285

His Glu Leu Arg Arg Arg Gly Val Asp Phe Gln Thr Leu Ala Leu Arg
                        290                 295                 300

Phe Val Gly Gln Trp Gln Lys Ala Ile Asp Tyr Ile Gly Asp Leu Ser
        305                 310                 315                 320

Val Leu Glu Ser Glu Leu Ser Met His Cys Glu Ile Val Lys Ser Leu
                        325                 330                 335

Ser Gly Tyr Arg Leu Ser Leu His Ser Gly Ser Asp Lys Phe Ser Val
                        340                 345                 350

Tyr Arg Ile Phe Thr His Tyr Cys Asp Gly Lys Leu His Val Lys Thr
                        355                 360                 365

Ala Gly Thr Ser Tyr Leu Glu Ala Ile Arg Thr Val Ala Glu Ala Ser
                        370                 375                 380

Pro Ser Leu Tyr Arg Asn Ile His Lys Tyr Ala Leu Thr Cys Phe Glu
        385                 390                 395                 400

Lys Asp Asn Thr Ser Tyr His Val Thr Ala Asp Ile Asn Lys Ile Pro
                        405                 410                 415

Asp Val Asp Asn Val Glu Asp Ser Lys Val Val Asn Leu Leu Asp Ile
                        420                 425                 430

Pro Glu Val Arg Gln Leu Ile His Ile Thr Tyr Gly Ser Val Leu Thr
                        435                 440                 445

Glu Lys Ile Asn Gly Lys Tyr Leu Phe Arg Asp Glu Ile Tyr Arg Ile
                        450                 455                 460

Leu His Glu Asn Glu Phe Leu His Tyr Lys Arg Ile Arg Asp His Leu
        465                 470                 475                 480

Gly Lys His Leu Glu Leu Leu Lys Asn
                        485

<210> SEQ ID NO 4
<211> LENGTH: 482
<212> TYPE: PRT
<213> ORGANISM: Thermoanaerobacter mathranii

<400> SEQUENCE: 4

Met Val Glu Lys Ser Ile Leu Glu Lys Leu Thr Asp Phe Leu Leu Asn
        1               5                   10                  15

His Ser Phe Val Leu Tyr Pro Asn Ser Leu Arg Lys Leu Lys Glu Asp
                        20                  25                  30

Thr Tyr Ile Phe Val Ala Lys Lys Asp Ala Lys Lys Ile Gly Ile
                        35                  40                  45

Leu Thr Lys Glu Asn Phe Lys Leu Thr Ser Pro Tyr Phe Val Glu Asp
                        50                  55                  60

Lys Asn Val Lys Glu Ile Asp Phe Tyr Leu Asn Leu Tyr Pro Leu Ser
        65                  70                  75                  80

Phe Glu Asn Tyr Leu Ile Leu Lys Asn Phe Gly Ile Ser Pro Thr Pro
                        85                  90                  95

Cys Arg Gln Lys Ser Ser Phe Gly Thr Gly Asp Arg Leu Gly Leu Val
                        100                 105                 110
```

```
Thr Pro Ala His Ile Val Ala Leu Lys Glu Tyr Pro Val Phe Pro Val
            115                 120                 125

Leu Ala Gln Gln Ser Pro Arg Glu Leu Glu Lys Thr His Arg Asp Phe
    130                 135                 140

Lys Asp Ala Leu Leu Lys Val Ile Leu Gly Val Leu Glu Ala Gly Tyr
145                 150                 155                 160

Thr Gly Glu Phe Gly Ala Asp Ala Asp His Ile Lys Asp Glu Lys Tyr
                165                 170                 175

Leu Leu Arg Ala Ile Glu Ala Gly Tyr Thr Met Tyr Thr Leu Asp Val
            180                 185                 190

Ser Glu Leu Leu Thr Lys Ile Leu Asp Ile Ser Ser Asn Gln Val Met
    195                 200                 205

Gln Ile Ser Pro Gln Ser Lys Glu Ile Ile Glu Ala Phe Lys Gly Lys
210                 215                 220

Lys Ile Ser Ile Ser Glu Glu Tyr Thr Ile Arg Glu Asp Glu Leu
225                 230                 235                 240

Tyr Lys Ser Ala Leu Ile Tyr Glu Lys Ala Met Asn Phe Val Glu Lys
                245                 250                 255

Val Tyr Ser Ile Leu Lys Glu Lys Val Lys Asp Phe Asp Leu Glu Ile
            260                 265                 270

Ser Ile Asp Glu Gly Glu Lys Asp Thr Thr Val Glu Asp His Ile Phe
    275                 280                 285

Val Ala Glu Tyr Leu His Lys Lys Gly Ile Asp Phe Trp Ser Leu Ala
290                 295                 300

Pro Lys Phe Pro Gly Glu Phe Gln Lys Ala Ile Asp Tyr Lys Gly Asp
305                 310                 315                 320

Ile Asn Lys Phe Ala Val Glu Leu Lys Lys His Tyr Ala Ile Ser Gln
                325                 330                 335

Gln Leu Gly Gly Tyr Lys Leu Ser Leu His Ser Gly Ser Asp Lys Phe
            340                 345                 350

Ser Ile Tyr Glu Ile Phe Ser Glu Val Thr Gln His Ser Phe His Ile
    355                 360                 365

Lys Thr Ser Gly Thr Ser Trp Leu Gln Ala Val Asn Leu Ile Phe Glu
370                 375                 380

Lys Asn Lys Lys Leu Phe Tyr Glu Leu Tyr Lys Ile Ala Leu Asn Asn
385                 390                 395                 400

Leu Glu Glu Ser Lys Lys Ala Tyr Lys Val Leu Ile Asp Lys Asp Asp
                405                 410                 415

Phe Ala Glu Glu Pro Asn Leu Glu Asn Val Gln Ile Leu Ser Gln Pro
            420                 425                 430

Glu Ile Lys Gln Leu Phe His Ile Ser Tyr Gly Val Leu Leu Asp Glu
    435                 440                 445

Lys Lys Glu Glu Ile Tyr Asp Val Leu Asp Lys Tyr Glu Glu His
450                 455                 460

Tyr Gln Phe Val Ser Ala Asn Ile Lys Asn His Leu Gly Lys Ile Phe
465                 470                 475                 480

Asn Asn

<210> SEQ ID NO 5
<211> LENGTH: 485
<212> TYPE: PRT
<213> ORGANISM: Dictyoglomus turgidum

<400> SEQUENCE: 5
```

```
Met Leu Lys Leu Leu Asn Glu Ser Leu Lys Pro Leu Ser Ile Phe Ile
1               5                   10                  15

Tyr Ser Glu Ser Leu Arg Lys Ile Asn Asp Asp Leu Tyr Ile Phe Val
                20                  25                  30

Ala Lys Ile Lys Asp Leu Lys Lys Ile Gly Ile Val Lys Gln Asn Gln
            35                  40                  45

Ile Leu Tyr Phe Ser Ser Pro Tyr Phe Ser Glu Asp Lys Lys Ile Glu
50                  55                  60

Gly Thr Asn Phe Leu Val Asn Leu Tyr Pro Leu Asn Phe Glu Asn Tyr
65                  70                  75                  80

Gln Lys Leu Lys Glu Ile Ile Pro Ile Ser Pro Lys Val Cys Asp Lys
                85                  90                  95

Lys Ile Ser Phe Gly Thr Gly Asp Arg Leu Gly Leu Ile Thr Ser Ala
            100                 105                 110

Gln Leu Ser Ala Leu Lys Glu Tyr Asp Leu Phe Pro Ile Leu Ala Gln
        115                 120                 125

Gln Ser Pro Arg Glu Leu Ile Lys Thr Lys Arg Asp Phe Lys Asp Val
    130                 135                 140

Leu Leu Lys Ser Ala Met Gly Val Leu Glu Thr Gly Tyr Thr Gly Lys
145                 150                 155                 160

Tyr Gly Ala Asp Ala Asp His Ile Lys Asp Glu Lys Tyr Leu Met Glu
                165                 170                 175

Ala Ile Asp Ala Gly Tyr Thr Met Tyr Thr Leu Asp Ile Ser Asp Phe
            180                 185                 190

Ile Glu Lys Ile Lys Asp Leu Ser Glu Lys Ala Leu Lys Glu Lys Tyr
        195                 200                 205

Glu Lys Val Ser Ser Phe Ser Lys Lys Ile Ile Asp Lys Tyr Ala Gly
    210                 215                 220

Lys Arg Val Lys Ile Ser Asp Glu Glu Tyr Phe Glu Leu Ser Tyr Asn
225                 230                 235                 240

Glu Leu Cys Lys Ser Ala Ile Val Tyr Glu Lys Ala Leu Ser Phe Val
                245                 250                 255

Glu Met Val Tyr Glu Ile Leu Lys Ser Lys Leu Ser Glu Phe Asp Ile
            260                 265                 270

Glu Val Ser Ile Asp Glu Gly Glu Arg Asp Thr Thr Pro Glu Asp His
        275                 280                 285

Phe Phe Val Ala Gln Phe Leu His Asp Lys Gly Ile Asp Phe Lys Ser
    290                 295                 300

Leu Ala Pro Lys Phe Pro Gly Glu Phe Gln Lys Gly Ile Asp Tyr Ile
305                 310                 315                 320

Gly Asp Ile Lys Glu Phe Glu Arg Ala Leu Lys Lys His Tyr Ala Leu
                325                 330                 335

Thr Lys Ala Leu Glu Gly Tyr Arg Leu Ser Leu His Ser Gly Ser Asp
            340                 345                 350

Lys Phe Ser Ile Tyr Lys Ile Phe Tyr Lys Ile Thr Glu Gly Asn Phe
        355                 360                 365

His Ile Lys Thr Ser Gly Thr Ser Trp Leu Glu Ala Val Lys Val Ile
    370                 375                 380

Ala Lys Phe Phe Pro Asp Leu Phe Val Glu Leu Tyr Gln Ile Ala Leu
385                 390                 395                 400

Glu Asn Leu Glu Glu Ser Lys Lys Ala Tyr Lys Val Asn Ile Thr Lys
                405                 410                 415

Glu Glu Phe Pro Lys Glu Ile Lys Glu Asp Tyr Met Glu Phe Leu His
```

```
                420             425             430
Lys Asp Asn Val Arg Gln Leu Phe His Ile Ser Tyr Gly Val Leu Leu
            435                 440                 445

Asp Glu Lys Arg Lys Glu Ile Tyr Asp Leu Leu Asn Gln Lys Glu Lys
            450                 455                 460

Glu His Tyr Gln Tyr Val Ser Glu Asn Ile Lys Lys His Leu Lys Asn
465                 470                 475                 480

Leu Phe Glu Glu Glu
                485

<210> SEQ ID NO 6
<211> LENGTH: 482
<212> TYPE: PRT
<213> ORGANISM: Thermoanaerobacterium xylanolyticum

<400> SEQUENCE: 6

Met Val Gly Asn Val Ser Ser Val Leu Lys Glu Ser Gly Phe Gln Ile
1               5                   10                  15

Tyr Pro Asp Ser Leu Arg Lys Leu Gly Glu Asn Thr Tyr Ile Phe Val
            20                  25                  30

Val Lys Lys Gln Lys Glu Lys Met Ile Gly Ile Leu Ser Asn Asp Glu
        35                  40                  45

Leu Lys Leu Lys Glu Pro Tyr Phe Ser Glu Asn Lys Lys Ile Ser Asp
50                  55                  60

Asn Leu Gln Phe Asn Val Tyr Ser Phe Thr Phe Asp Asn Tyr Val Thr
65                  70                  75                  80

Leu Asn Gly Arg Phe His Ile Gly Pro Thr Ile Cys Arg Glu Asn Ala
                85                  90                  95

Ser Phe Gly Thr Gly Asp Arg Leu Gly Leu Ala Thr Ala Ala Gln Leu
            100                 105                 110

Asp Ala Leu Lys Lys Phe Asn Val Phe Pro Ile Leu Ala Gln Gln Ser
        115                 120                 125

Pro Arg Glu Leu Val Lys Thr Asn Arg Asp Phe Lys Asp Val Leu Leu
130                 135                 140

Lys Val Val Leu Gly Val Leu Glu Thr Gly Tyr Ile Gly His Tyr Gly
145                 150                 155                 160

Ala Asp Ala Asp His Ile Lys Asp Glu Lys Tyr Leu Leu Glu Gly Ile
                165                 170                 175

Asp Ala Gly Tyr Thr Met Tyr Thr Leu Asp Leu Ser Glu Gln Leu Phe
            180                 185                 190

Asp Val Ser Gly Ala Thr Ser Leu Glu Ile Lys Glu Lys Ala Lys Thr
        195                 200                 205

Leu Ser Asp Val Ser Arg Lys Ile Val Glu Asp Phe Ser Gly Lys Ser
210                 215                 220

Leu Asn Val Gly Phe Gly Gly His Leu Val Ser Glu Asp Glu Leu Leu
225                 230                 235                 240

Lys Ser Ala Val Ala Tyr Glu Ala Ala Met Lys Phe Val Glu Lys Val
                245                 250                 255

Asn Asp Ile Leu Lys Glu Lys Leu Asn Asp Phe Asp Leu Glu Ile Ser
            260                 265                 270

Ile Asp Glu Gly Gly Lys Val Thr Thr Leu Glu Asp His Leu Phe Val
        275                 280                 285

Ala Glu Tyr Leu His Arg Asn Gly Ile Asp Phe Ser Ile Ala Pro
290                 295                 300
```

```
Lys Phe Pro Gly Glu Phe Glu Lys Ala Ile Asp Tyr Val Gly Asp Val
305                 310                 315                 320

Asn Glu Phe Glu Arg Glu Leu Lys Lys His Tyr Asp Leu Thr Lys Leu
            325                 330                 335

Ile Gly Gly Tyr Lys Leu Ser Leu His Ser Gly Ser Asp Lys Phe Ser
            340                 345                 350

Ile Tyr Lys Ile Phe Ser Gln Thr Thr Glu Lys Asn Phe His Ile Lys
            355                 360                 365

Thr Ser Gly Thr Ser Trp Leu Gln Ala Val Asn Leu Ile Tyr Lys Ser
            370                 375                 380

Asp Lys Glu Phe Tyr Arg Glu Leu Tyr Lys Ile Ala Leu Ser Asn Leu
385                 390                 395                 400

Glu Glu Ser Lys Lys Ser Tyr Lys Val Leu Ile Lys Lys Asp Asp Phe
            405                 410                 415

Lys Asp Glu Pro Glu Leu Asp Asn Ser Glu Phe Ile Ile Arg Pro Glu
            420                 425                 430

Ile Lys Gln Leu Phe His Ile Ser Phe Gly Val Leu Leu Asp Leu Lys
            435                 440                 445

Gly Lys Glu Ile Lys Asp Met Leu Tyr Asp Tyr Glu Glu Glu His Tyr
450                 455                 460

Lys Met Val Ser Asp Asn Ile Glu Asn His Leu Lys Glu Ile Phe Tyr
465                 470                 475                 480

Glu Lys

<210> SEQ ID NO 7
<211> LENGTH: 483
<212> TYPE: PRT
<213> ORGANISM: Thermoanaerobacter siderophilus

<400> SEQUENCE: 7

Met Lys Glu Glu Leu Ser Asp Tyr Leu Leu Lys Asn Ser Phe Leu Leu
1               5                   10                  15

Tyr Pro Asp Ser Phe Arg Arg Leu Arg Glu Asp Val Tyr Ile Phe Val
            20                  25                  30

Ala Lys Lys Asp Ser Asp Lys Lys Ile Gly Leu Leu Thr Asn Gly Asn
        35                  40                  45

Phe Lys Leu Ser Ser Pro His Phe Ala Glu Asp Lys Tyr Val Glu Glu
50                  55                  60

Leu Gly Phe Tyr Ile Asn Leu Tyr Pro Leu Thr Tyr Glu Asn Tyr Leu
65                  70                  75                  80

Ile Leu Lys Asp Asn Phe Gly Ile Ser Pro Val Thr Cys Lys Glu Lys
                85                  90                  95

Ala Ser Phe Gly Thr Gly Asp Arg Leu Gly Leu Ala Thr Pro Ala His
            100                 105                 110

Ile Lys Ala Leu Lys Asn Tyr Asn Val Phe Pro Val Leu Ala Gln Gln
        115                 120                 125

Ser Pro Arg Glu Leu Val Lys Thr His Arg Asp Phe Lys Asp Val Phe
130                 135                 140

Leu Lys Val Ile Leu Gly Val Leu Glu Ala Gly Tyr Ala Gly Gly Tyr
145                 150                 155                 160

Gly Ala Asp Ala Asp His Ile Lys Asp Glu Lys Tyr Leu Ile Glu Ala
                165                 170                 175

Ile Asp Ala Gly Tyr Thr Met Tyr Thr Leu Asp Leu Ser Asp Leu Leu
            180                 185                 190
```

```
                -continued

Val Lys Ile Ser Asp Met Pro Lys Ser Gln Leu Lys Glu Lys Ala Gln
            195                 200                 205

Ser Leu Ser Ser Gln Ser Arg Glu Ile Ile Asp Arg Phe Lys Gly Lys
        210                 215                 220

Lys Phe Ser Ile Ser Thr Asp Glu Asp Phe Ala Val Ser Glu Asp Glu
225                 230                 235                 240

Leu Tyr Lys Ser Ala Leu Thr Tyr Glu Lys Ala Met Lys Phe Val Glu
                245                 250                 255

Lys Val Tyr Gly Ile Leu Lys Asp Arg Leu Gln His Phe Asp Leu Glu
            260                 265                 270

Ile Ser Ile Asp Glu Gly Glu Lys Asp Thr Thr Val Glu Asp His Ile
        275                 280                 285

Phe Val Ala Glu Tyr Leu His Arg Lys Gly Ile Asp Phe Trp Ser Leu
        290                 295                 300

Ala Pro Lys Phe Pro Gly Glu Phe Gln Lys Ala Ile Asp Tyr Lys Gly
305                 310                 315                 320

Asp Ile Lys Lys Phe Thr Ser Gly Leu Lys Lys His Tyr Phe Leu Ser
                325                 330                 335

Lys Lys Leu Gly Gly Tyr Lys Leu Ser Leu His Ser Gly Ser Asp Lys
            340                 345                 350

Phe Ser Ile Tyr Lys Ile Phe Asn Glu Ile Thr Glu Gly Asn Phe His
        355                 360                 365

Ile Lys Thr Ser Gly Thr Ser Trp Leu Gln Ala Ile Asn Ile Ile Phe
        370                 375                 380

Glu Arg Asp Lys Asp Leu Phe Asn Asp Leu Tyr Lys Ile Ala Leu Asp
385                 390                 395                 400

Asn Leu Glu Glu Ser Lys Lys Ala Tyr Lys Val Leu Ile Asp Arg Asp
                405                 410                 415

Asp Phe Pro Gln Thr Ile Gln Thr Glu Asp Ser Gln Ile Leu Leu Lys
                420                 425                 430

Pro Glu Ile Lys Gln Leu Phe His Ile Ser Tyr Gly Val Leu Leu Asp
            435                 440                 445

Glu Arg Arg Lys Glu Ile Tyr Glu Val Leu Asn Lys Tyr Glu Glu Glu
        450                 455                 460

His Tyr Glu Phe Val Ser Lys Asn Ile Glu Asn His Leu Lys Glu Ile
465                 470                 475                 480

Phe Asn Ile
```

COMPOSITION FOR PREPARING TAGATOSE AND METHOD FOR PREPARING TAGATOSE FROM FRUCTOSE

TECHNICAL FIELD

The present invention relates to a composition for preparing tagatose and a method for preparing tagatose from fructose, and more particularly, to a gene encoding a thermophilic fructose 4-epimerase derived from thermophilic microorganisms and a method for preparing tagatose from fructose using the enzyme.

BACKGROUND ART

Tagatose is an epimer of D-fructose, and has a natural sweet taste hardly distinguishable from sucrose and physical properties similar to sucrose. Tagatose is a natural sweetener, which is present in a small amount in food such as milk, cheese, cacao, and the like, and in sweet fruits such as apples and mandarin. Tagatose has a calorie value of 1.5 kcal/g which is one third that of sucrose, and a glycemic index (GI) of 3 which is 5% that of sucrose. Tagatose has a sweet taste similar to that of sucrose and various health benefits. In this regard, tagatose can be used as an alternative sweetener capable of satisfying both taste and health when applied to a wide variety of products.

It is known that tagatose can be produced from galactose by a chemical (catalytic reaction) method or a biological (isomerizing enzyme reaction) method (Korean Patent Laid-open Publication No. 2009-0082774, published on Jul. 31, 2009). In order to economically produce galactose as a raw material for the above reactions, studies have been made to develop various raw materials containing galactose, a method for attaining galactose and a method for producing tagatose using the raw materials. Lactose has been used as the most representative raw material for galactose. However, the price of lactose or lactose-containing products was unstable, depending on produced amounts, supply and demand of raw milk and lactose in global markets, and the like. Such price fluctuations disrupt stable supply of raw materials for producing tagatose.

Specifically, around 2012, sharp increase in global lactose price was mainly caused by rapid demand for skimmed milk powder and whole milk powder containing lactose due to rapid economic growth in China and decrease in annual milk production in dairy-producing countries due to global warming. Such price fluctuations in raw material price make stable production of tagatose difficult. Accordingly, there is a need for a new method for preparing tagatose using common saccharides (sucrose, glucose, fructose, and the like).

DISCLOSURE

Technical Problem

In the past, tagatose was produced using galactose decomposed from various biological resources such as whey permeate which is a soluble byproduct as food raw materials except lactose, and larch which is plant biomass.

However, there are no suitable raw materials capable of being commercially produced or approaching commercialization in terms of stable supply of raw materials and investment efficiency.

It is one object of the present invention to provide a composition for preparing tagatose from common saccharides more suitable for industrial applications than prior methods for preparing tagatose from galactose, and a method for preparing tagatose.

Specifically, the present invention is aimed at providing a novel enzyme protein, the function of which is not elucidated in the prior art, and which has D-fructose 4-epimerase activity and is capable of preparing tagatose in high yield from fructose, a gene encoding the same, a composition for preparing tagatose using the same and a method for preparing tagatose from fructose.

Technical Solution

One embodiment of the present invention provides a composition for preparing tagatose from fructose, including: a protein having an amino acid sequence of SEQ ID NO: 1 to SEQ ID NO: 7 or a microorganism expressing the protein.

Another embodiment of the present invention provides a method for preparing tagatose from fructose, including: reacting the composition of the present invention with fructose.

Advantageous Effects

The present invention can provide a method for producing tagatose, which is economical and has high yield using a common raw material, fructose, by developing a novel D-fructose 4-epimerase which has an activity for producing tagatose by epimerizing fructose at carbon number 4.

In addition, the present invention can provide a method for producing tagatose, which is economical and has high yield using a common raw material, fructose, instead of lactose with violent price fluctuations, thereby reducing production costs.

In general, since it is well known in the art that fructose can be industrially produced from glucose or sucrose, raw materials suggested in the present invention encompass not only fructose but also raw materials entirely or partially containing fructose such that more economical production can be ensured. Namely, the present invention encompasses production of tagatose through enzymatic conversion of starch, crude sugar or sucrose.

Further, the present invention can produce tagatose from fructose, which ensures efficient mass production of tagatose attracting attention as an important food material today.

DESCRIPTION OF DRAWINGS

FIG. 5a to FIG. 5g show graphs depicting activity of seven D-fructose 4-epimerases derived from each of thermophilic microorganisms, depending on kinds of metal ions.

FIG. 6a to FIG. 6g show amino acid sequences of proteins set forth in SEQ ID NO: 1 to SEQ ID NO: 7 derived from each of seven thermophilic microorganisms.

EMBODIMENTS

Figure 1A:
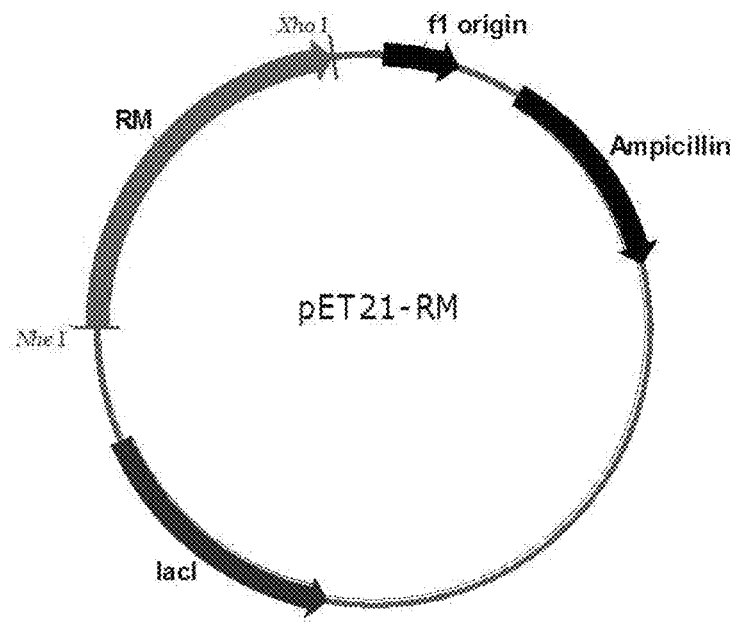
FIG. 1a to FIG. 1g show cleavage maps of recombinant vectors for expressing seven D-fructose 4-epimerases derived from each of thermophilic microorganisms.

Hereinafter, the present invention will be described in more detail based on concrete embodiments. The present invention are not intended as limitations by the embodiments. Descriptions of details apparent to those skilled in the art having ordinary knowledge in this technical field or relevant field will be omitted herein.

As used herein, the term "carbon at n-position (hereinafter referred to as Cn)" refers to a carbon position defined in accordance with IUPAC nomenclature, wherein n is an integer of 1 or more. For example, "epimerization at carbon 4 position" is expressed as "C4-epimerization".

One embodiment of the present invention provides a composition for preparing tagatose from fructose, which includes: a protein having an amino acid sequence set forth in SEQ ID NO: 1 to SEQ ID NO: 7 or a microorganism expressing the protein.

Generally, monosaccharides can be classified into aldohexoses and ketohexoses. An aldohexose refers to an aldose that has six carbon atoms and an aldehyde group at one end thereof. Examples of the aldohexose include glucose, galactose, allose, gulose, altrose, mannose, talose, and idose, without being limited thereto.

Further, a ketohexose refers to a monosaccharide having six carbon atoms and a ketone group. Examples of the ketohexose include fructose, tagatose, psicose, and sorbose, without being limited thereto. Specifically, fructose is used as a ketohexose. As used herein, both fructose and tagatose refer to D-fructose and D-tagatose, unless otherwise specified.

In one embodiment of the present invention, an amino acid sequence set forth in SEQ ID NO: 1 to SEQ ID NO: 7 may be an enzyme which has an activity for producing tagatose by epimerizing fructose at carbon number 4.

Specifically, the present inventors utilized microorganisms belonging to thermophile genus *Rhodothermus*, genus *Thermoanaerobacter*, genus *Thermotoga*, and genus *Dictyoglomus*. Since enzymes produced from thermophilic microorganisms have the same functions as enzymes produced from mesophilic microorganisms, can stably perform reaction under extreme conditions (high temperature or the like), can prevent contamination by mesophilic microorganisms, can increase solubility of materials having low solubility in substrates, and can increase reaction rate, the enzymes produced from thermophilic microorganisms can overcome industrial disadvantages of mesophilic enzymes. The present inventors screened fructose 4-epimerases from the aforementioned thermophilic microorganisms and then, among their native genes, finally identified for novel polynucleotides, which express enzymes capable of converting fructose to tagatose. The present invention provides an enzyme converting fructose to tagatose by synthesizing a polynucleotide sequence optimized to effectively over-express a protein, inserting the polynucleotide into a recombinant vector, and expressing an enzyme.

An amino acid sequence set forth in SEQ ID NO: 1 to SEQ ID NO: 7 may be transformed by a recombinant vector including a gene encoding a protein having the above sequence.

Examples of microorganisms for transformation include *Escherichia. coli*, (hereinafter referred to as *E. coli*), *Corynebacterum glutamicum, Aspergillus oryzae*, or *Bacillus subtilis*, and the like. Examples of microorganisms transformed by *E. coli* may include *Escherichia coli* BL21 (DE3)-pET21a-RM (accession number: KCCM11576P), *Escherichia coli* BL21(DE3)-pET21a-TAM (accession number: KCCM11577P), *Escherichia coli* BL21(DE3)-pET21a-TAS (accession number: KCCM11578P), *Escherichia coli* BL21(DE3)-pET21a-TAX (accession number: KCCM11579P), *Escherichia coli* BL21(DE3)-pET21a-TP (accession number: KCCM11580P), *Escherichia coli* BL21 (DE3)-pET21a-TL (accession number: KCCM11581P), and *Escherichia coli* BL21(DE3)-pET21a-DT (accession number: KCCM11582P), which were deposited at the Korean Culture Center of Microorganisms (KCCM) (361-221 Hongje 1-dong, Seodaemun-gu, Seoul, Korea) on Oct. 6, 2014 as accession numbers KCCM11576P, KCCM11577P, KCCM11578P, KCCM11579P, KCCM11580P, KCCM11581P, and KCCM11582P, respectively.

Specifically, in one embodiment, a protein having an amino acid sequence set forth in SEQ ID NO: 1 may be an enzyme derived from *Rhodothermus marinus*.

The protein may have a molecular weight of 55 kDa to 60 kDa, an optimum activity temperature of 50° C. to 90° C., and an optimum activity pH of 6.0 to 9.0.

More specifically, the optimum activity temperature may be 60° C. to 80° C., and the optimum activity pH may be 7.0 to 9.0.

Specifically, in one embodiment, a protein having an amino acid sequence set forth in SEQ ID NO: 2 may be an enzyme derived from *Thermotoga petrophila*.

The protein may have a molecular weight of 55 kDa to 58 kDa, an optimum activity temperature of 50° C. to 90° C., and an optimum activity pH of 7.0 to 9.0.

More specifically, the optimum activity temperature may be 70° C. to 90° C.

Specifically, in one embodiment, a protein having an amino acid sequence set forth in SEQ ID NO: 3 may be an enzyme derived from *Thermotoga lettingae*.

The protein may have a molecular weight of 55 kDa to 58 kDa, an optimum activity temperature of 50° C. to 90° C., and an optimum activity pH of 7.0 to 9.0.

More specifically, the optimum activity temperature may be 60° C. to 80° C.

Specifically, in one embodiment, a protein having an amino acid sequence set forth in SEQ ID NO: 4 may be an enzyme derived from *Thermoanaerobacter mathranii*.

The protein may have a molecular weight of 55 kDa to 58 kDa, an optimum activity temperature of 50° C. to 90° C., and an optimum activity pH of 7.0 to 10.0.

More specifically, the optimum activity temperature may be 70° C. to 90° C. and the optimum activity pH may be 8.0 to 10.0.

Specifically, in one embodiment, a protein having an amino acid sequence set forth in SEQ ID NO: 5 may be an enzyme derived from *Dictyoglomus turgidum*.

The protein may have a molecular weight of 55 kDa to 58 kDa, an optimum activity temperature of 50° C. to 90° C., and an optimum activity pH of 7.0 to 9.0.

More specifically, the optimum activity temperature may be 60° C. to 80° C.

Specifically, in one embodiment, a protein having an amino acid sequence set forth in SEQ ID NO: 6 may be an enzyme derived from *Thermoanaerobacterium xylanolyticum*.

The protein may have a molecular weight of 53 kDa to 58 kDa, an optimum activity temperature of 50° C. to 90° C., and an optimum activity pH of 6.0 to 9.0.

More specifically, the optimum activity temperature may be 60° C. to 80° C. and the optimum activity pH may be 6.0 to 8.0.

Specifically, in one embodiment, a protein having an amino acid sequence set forth in SEQ ID NO: 7 may be an enzyme derived from *Thermoanaerobacter siderophilus*.

The protein may have a molecular weight of 55 kDa to 58 kDa, an optimum activity temperature of 50° C. to 80° C., and an optimum activity pH of 7.0 to 10.0.

More specifically, the optimum activity temperature may be 60° C. to 80° C. and the optimum activity pH may be 8.0 to 10.0.

Another embodiment of the present invention provides a method for preparing tagatose from fructose, which includes: reacting a composition according to any one of embodiments of the present invention with fructose.

Specifically, the reaction may be performed at 50° C. to 80° C.

Further, the reaction may be performed at pH 6.0 to 9.0.

In addition, the reaction may be performed by further adding magnesium ions, zinc ions, nickel ions, cobalt ions, iron ions, manganese ions, or a mixture thereof.

Furthermore, as a substrate, fructose may be present in a concentration of 5% (w/v) to 60% (w/v).

According to one embodiment of the present invention, fructose may be obtained from sucrose or glucose. As a result, the present invention can provide a method for producing tagatose in high yield using common and inexpensive raw materials such as glucose, fructose, sucrose, and the like, which enables mass production of tagatose.

Accordingly, the present invention may further include hydrolyzing sucrose or isomerizing glucose to produce fructose prior to reaction of the composition according to any one of embodiments of the present invention with fructose.

Enzymes utilized in hydrolysis may be at least one selected from the group consisting of β-D-fructosidase including β-fructofuranosidase, invertase, saccharase, and the like; sucrase, α-glucosidase, and α-D-glucohydrolase, without being limited thereto.

Examples of the enzyme isomerizing glucose may include glucose isomerase and phosphogluco isomerase, without being limited thereto.

EXAMPLE

Figure 1B:
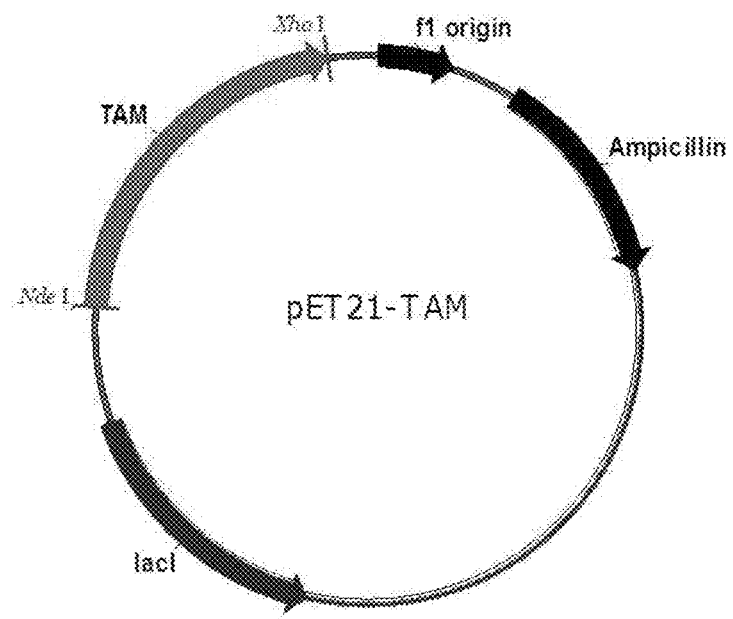
Figure 1C:
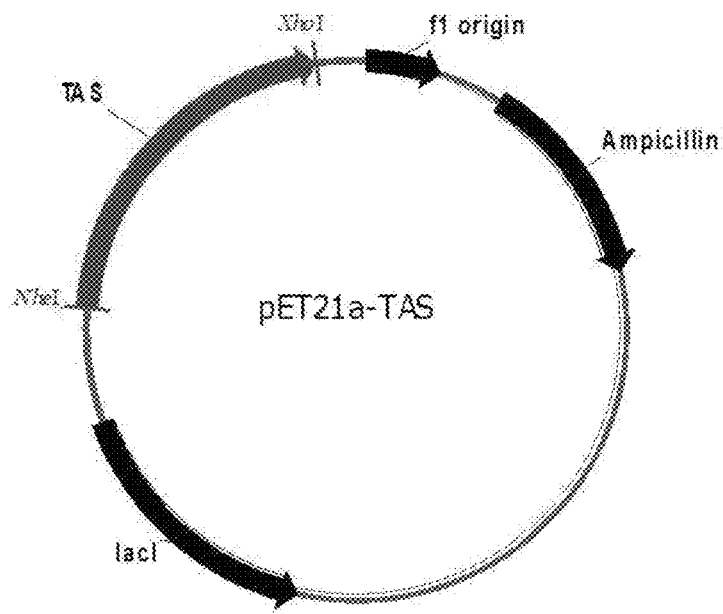
Figure 1D:
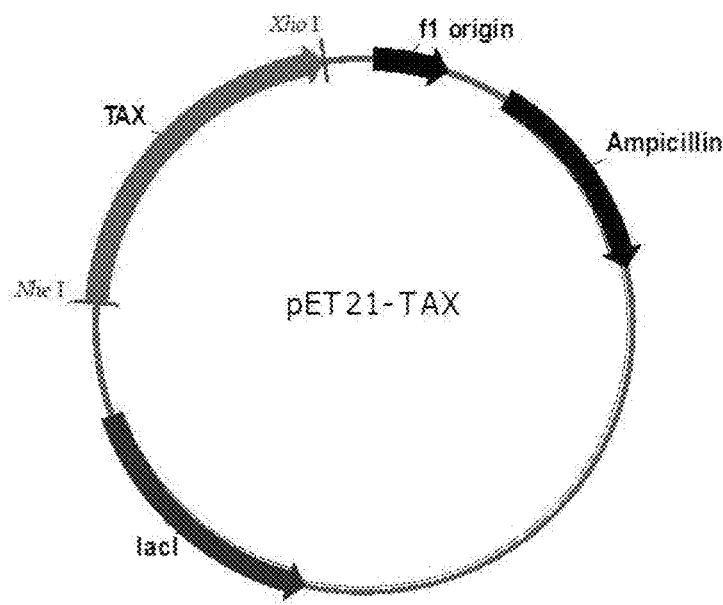
Figure 1E:
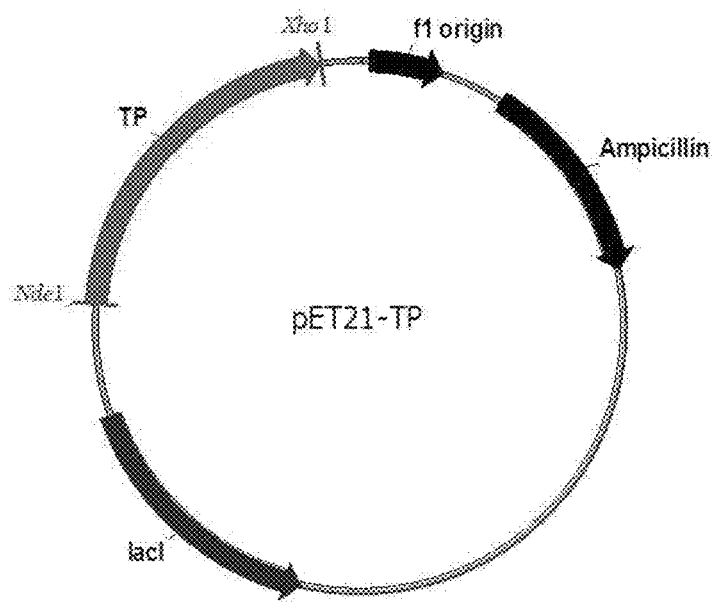
Figure 1F:
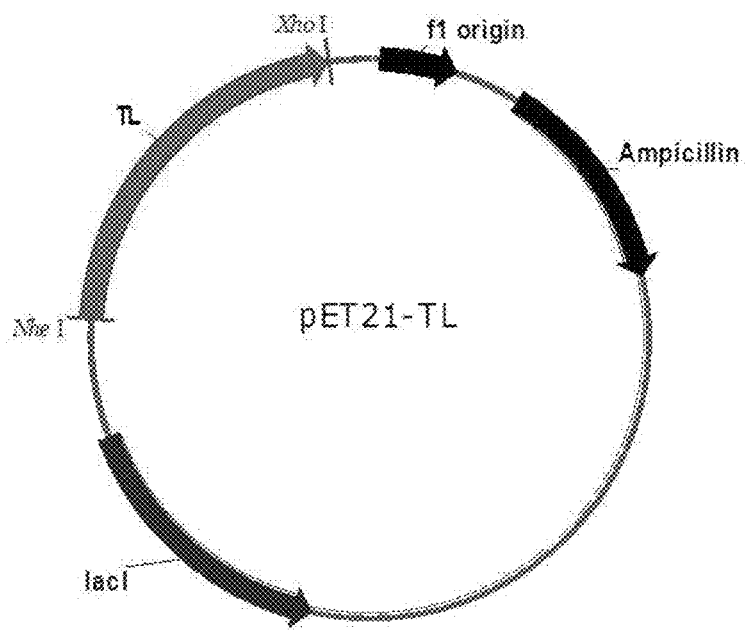
Figure 1G:
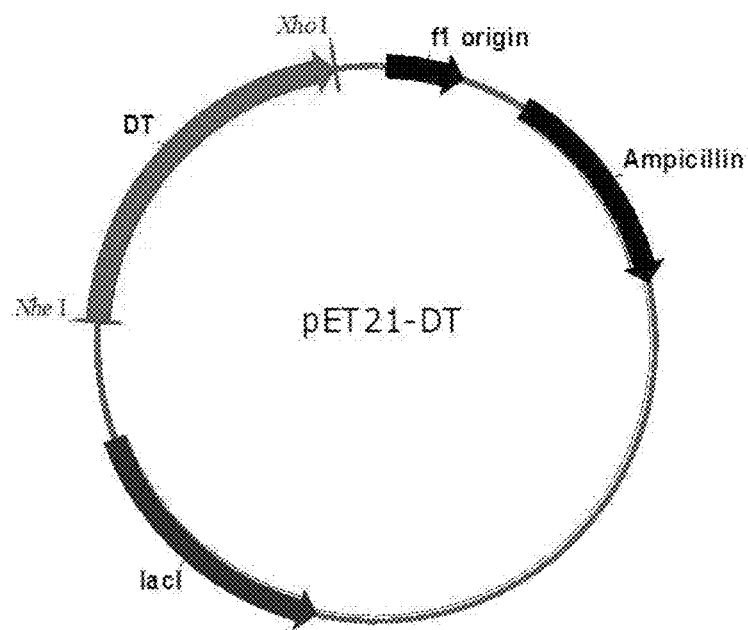

Example 1. Preparation of a Recombinant Microorganism Producing D-Fructose 4-Epimerase Polynucleotides encoding amino acid sequences set forth in SEQ ID NO: 1 to SEQ ID NO: 7 (FIG. 6a to FIG. 6g) shown in Table 1 derived from seven thermophilic microorganisms were inserted into a restriction site in an expression vector pET21a (Novagen) using restriction enzymes NdeI and XhoI, thereby preparing recombinant vectors pET21a-RM, pET21a-TAM, pET21a-TAS, pET21a-TAX, pET21a-TP, pET21a-TL, and pET21a-DT (FIG. 1a to FIG. 1g). The recombinant vectors were subjected to a heat shock method (Sambrook and Russell: Molecular Cloning) to transform *E. coli* BL21(DE3) (Invitrogen), thereby preparing a recombinant microorganism.

TABLE 1

| | List of Thermophilic Microorganism |
|---|---|
| RM | *Rhodothermus marinus* |
| TAM | *Thermoanaerobacter mathranii* |
| TAS | *Thermoanaerobacter siderophilus* SR4 |
| TAX | *Thermoanaerobacterium xylanolyticum* |

TABLE 1-continued

| | List of Thermophilic Microorganism |
|---|---|
| TP | *Thermotoga petrophila* |
| TL | *Thermotoga lettingae* |
| DT | *Dictyoglomus turgidum* |

The transformed recombinant microorganism was inoculated to 5 ml LB-ampicillin medium (Difco), cultured by shaking at 37° C. and 180 rpm until absorbance (OD) at 600 nm reached 1.5, and was then inoculated to a 500 ml LB-ampicillin medium. Then, 5 mM lactose was added to the resulting mass in order to induce overexpression of the target enzyme, followed by culturing in a shaking incubator at 37° C. The cultivation conditions were maintained at 37° C. and 180 rpm for 16 hours. Thereafter, the resulting mass was centrifuged in a centrifuge at 4,000 rpm for 20 minutes to collect only recombinant microorganisms.

Thus prepared recombinant microorganisms were named as *Escherichia coli* BL21(DE3)-pET21a-RM (accession number: KCCM11576P), *Escherichia coli* BL21(DE3)-pET21a-TAM (accession number: KCCM11577P), *Escherichia coli* BL21(DE3)-pET21a-TAS (accession number: KCCM11578P), *Escherichia coli* BL21(DE3)-pET21a-TAX (accession number: KCCM11579P), *Escherichia coli* BL21(DE3)-pET21a-TP (accession number: KCCM11580P), *Escherichia coli* BL21(DE3)-pET21a-TL (accession number: KCCM11581P), and *Escherichia coli* BL21(DE3)-pET21a-DT (accession number: KCCM11582P), which were deposited at the Korean Culture Center of Microorganisms (KCCM) (361-221 Hongje 1-dong, Seodaemun-gu, Seoul, Korea) on Oct. 6, 2014 as accession numbers KCCM11576P, KCCM11577P, KCCM11578P, KCCM11579P, KCCM11580P, KCCM11581P, and KCCM11582P, respectively.

Example 2. Purification and Property Identification of D-Fructose 4-Epimerase 2-1. Purification of D-Fructose 4-Epimerase Seven microorganisms collected in Example 1 were dissolved in a lysis buffer (50 mM K-phosphate) and then were disrupted using an Ultrasonic processor at 4° C. for 10 minutes. The disrupted liquid was subjected to heat treatment in a shaking incubator at 60° C. for 30 minutes, followed by centrifuging at 13,000 rpm for 10 minutes to obtain supernatants. The obtained supernatants were applied to a Q-Sepharose DEAE equilibrated with the lysis buffer, followed by sequentially flowing 50 mM K-phosphate and a buffer solution containing 200 mM NaCl, thereby purifying the intended proteins. The eluted proteins were dialyzed with a buffer solution for enzyme activity evaluation (50 mM K-phosphate, pH 7), which was then used in the next experiment. Further, seven purified D-fructose 4-epimerases, RM, TAM, TAS, TAX, TP, TL, and DT were subjected to sodium dodecyl sulfate polyacrylamide gel electrophoresis (SDS-PAGE) and found to have a molecular weight of about 58 kDa, 56 kDa, 56 kDa, 55 kDa, 56 kDa, 57 kDa, and 57 kDa, respectively.

2-2. Activity Analysis of D-Fructose 4-Epimerase Depending on Changes in Temperature and pH In order to identify activity of seven D-fructose 4-epimerases purified in Example 2-1 depending on changes in pH and temperature, the enzymes were reacted with fructose substrate at varying pH and temperature.

Activity measurement was performed by reacting 50 mM fructose, 1 mg/ml of enzymes, and 0.1 mM NiSO$_4$ at each pH and temperature range, followed by quenching the reaction product with ice, and then analyzed by HPLC. HPLC analysis was performed using a SUGAR SP0810 (Shodex) column at 80° C. while flowing water as a mobile phase at a flow rate of 0.6 ml/min, followed by detecting tagatose using a Differential Refractive Index Detector to analyze tagatose productivity.

Figure 3A:
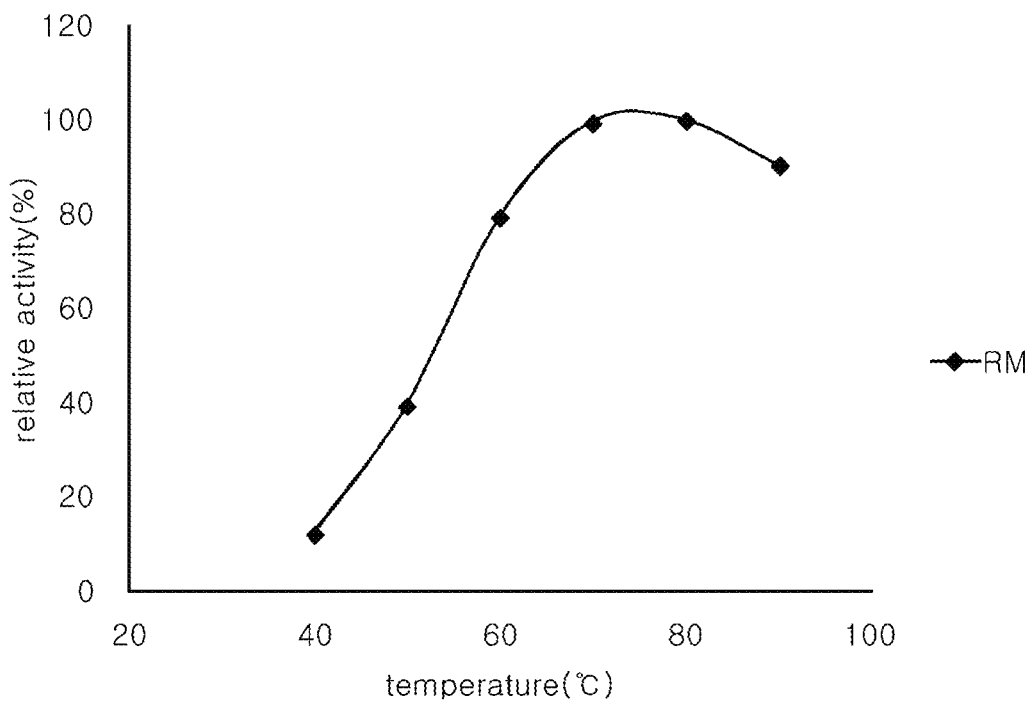
FIG. 3a to FIG. 3g show graphs depicting activity of seven D-fructose 4-epimerases derived from each of thermophilic microorganisms, depending on temperature.
Figure 3B:
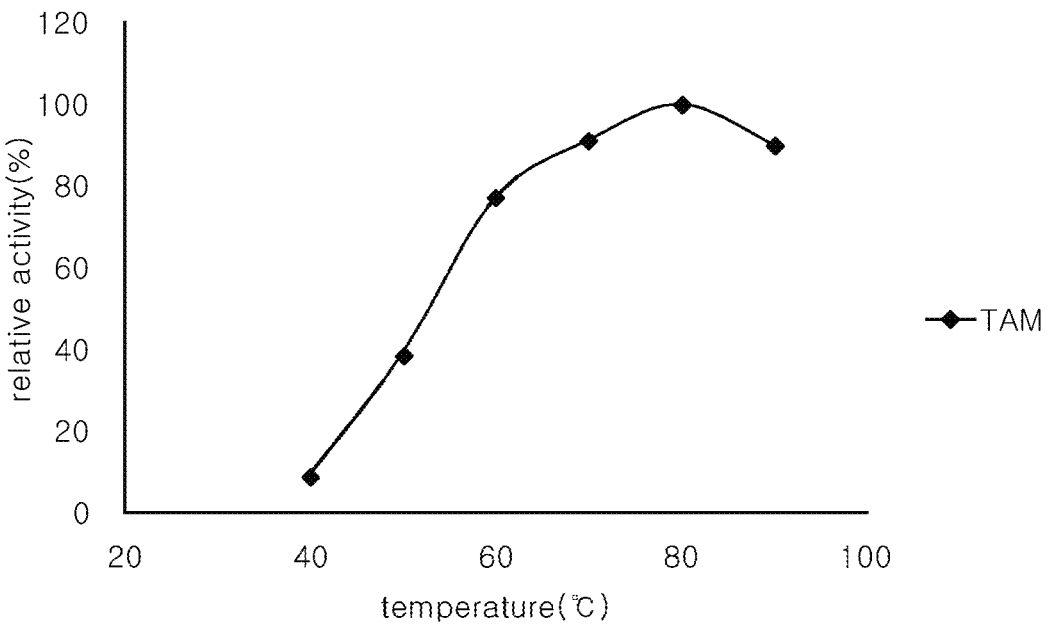
Figure 3C:
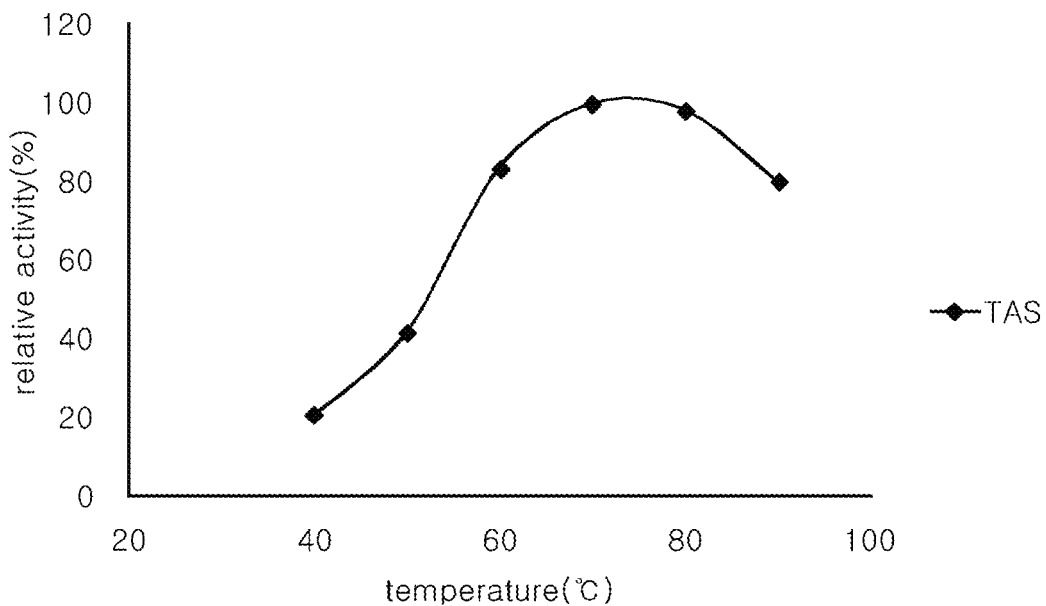
Figure 3D:
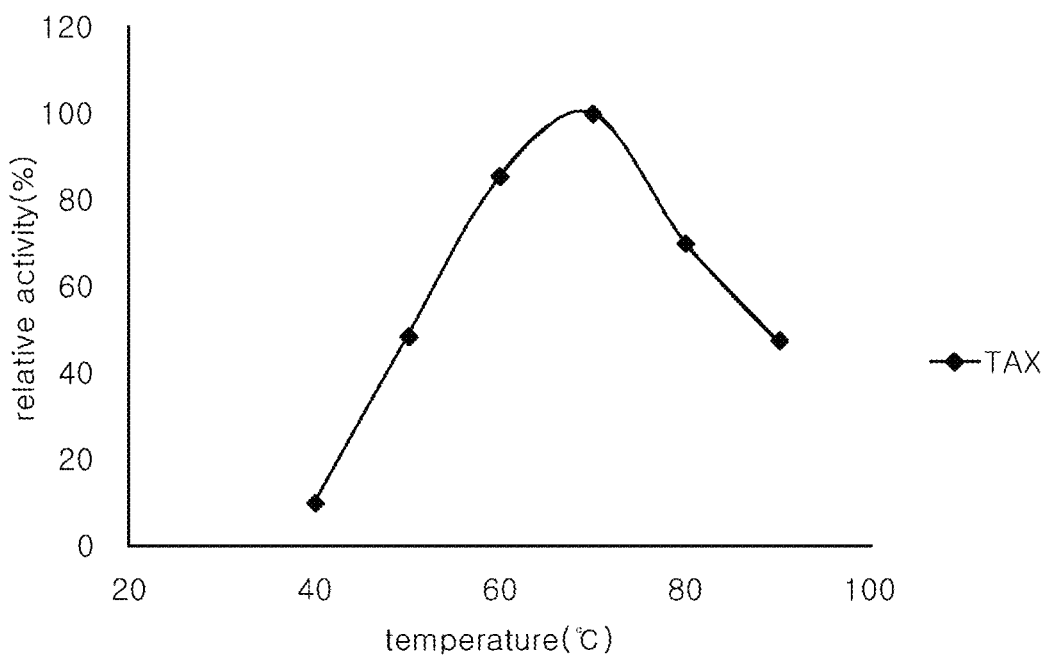
Figure 3E:
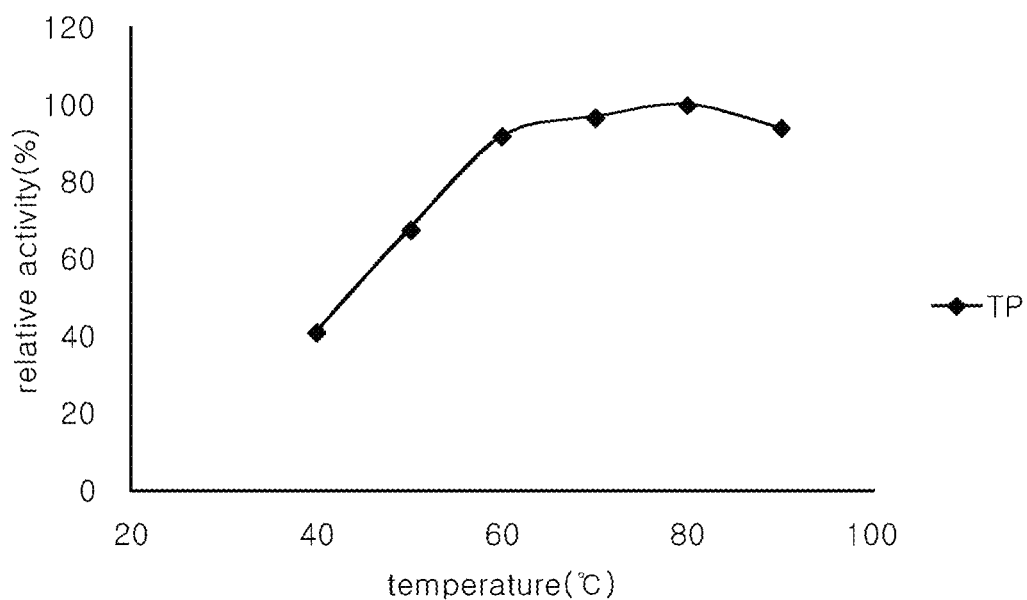
Figure 3F:
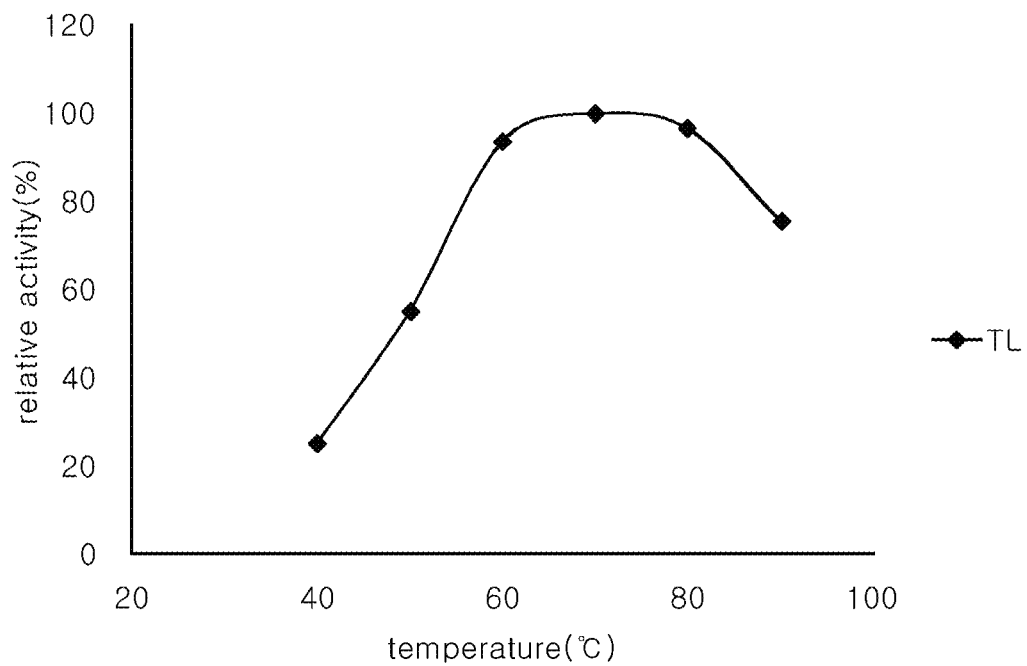
Figure 3G:
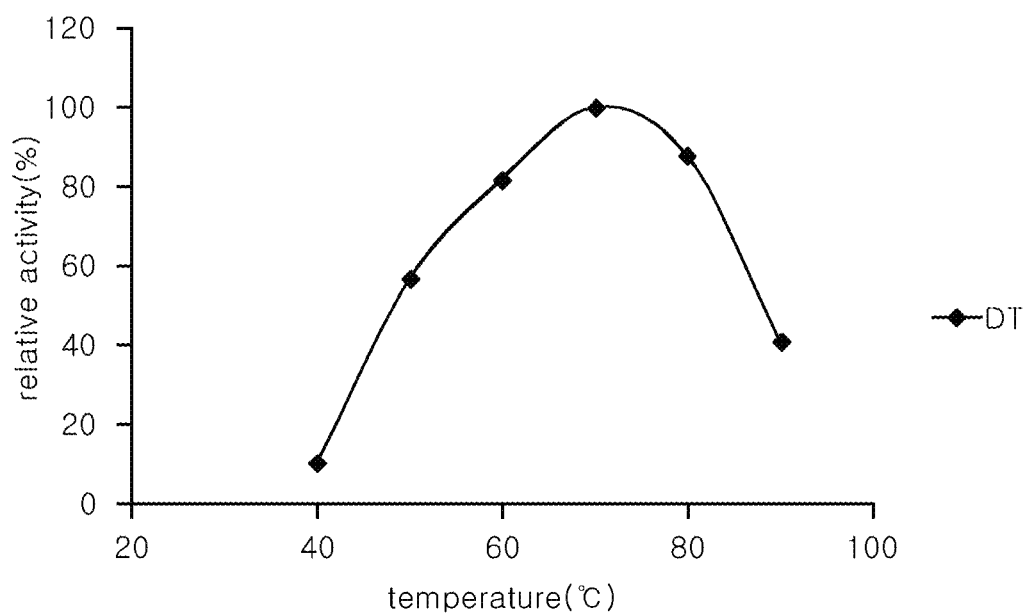

First, in order to evaluate activity of enzymes at pH 7 depending on temperature change, tagatose productivity was measured at 40° C. to 90° C. As a result, among seven enzymes, two enzymes TAM and TP showed maximum conversion rate at 80° C. while five enzymes RM, TAS, TAX, TL, and DT showed maximum conversion rate at 70° C. (FIG. 3a to FIG. 3g).

Further, in order to evaluate activity of enzymes depending on pH change, tagatose productivity was measured at 70° C. using buffer solutions of 50 mM sodium acetate pH 4-6, 50 mM K-phosphate pH 6-8, and 50 mM Tris-HCl pH 7 to pH 9, respectively. As a result, it was confirmed that the enzymes demonstrated maximum activity at different pH values, specifically high activity at pH 7 to pH 9.

Figure 4A:
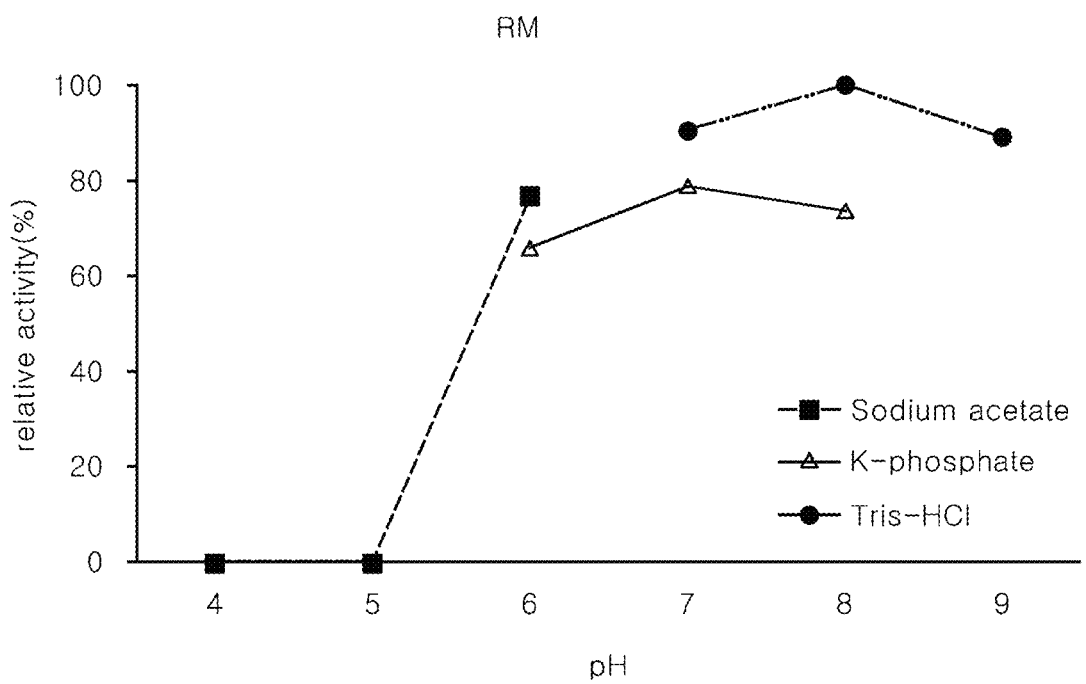
FIG. 4a to FIG. 4g show graphs depicting activity of seven D-fructose 4-epimerases derived from each of thermophilic microorganisms, depending on pH change.
Figure 4B:
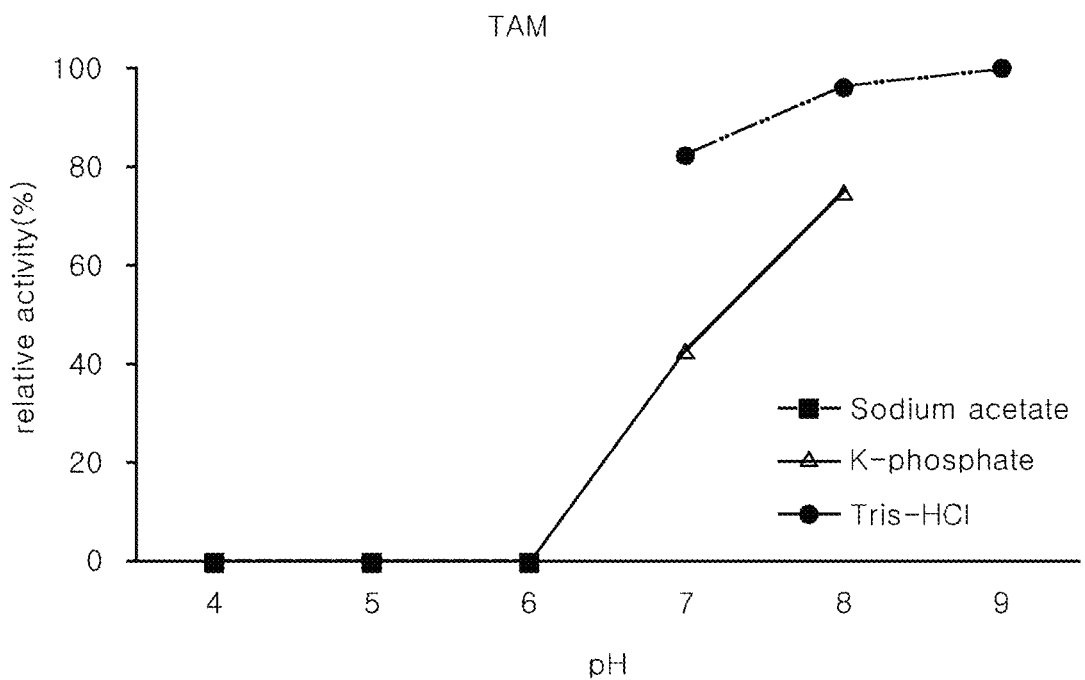
Figure 4C:
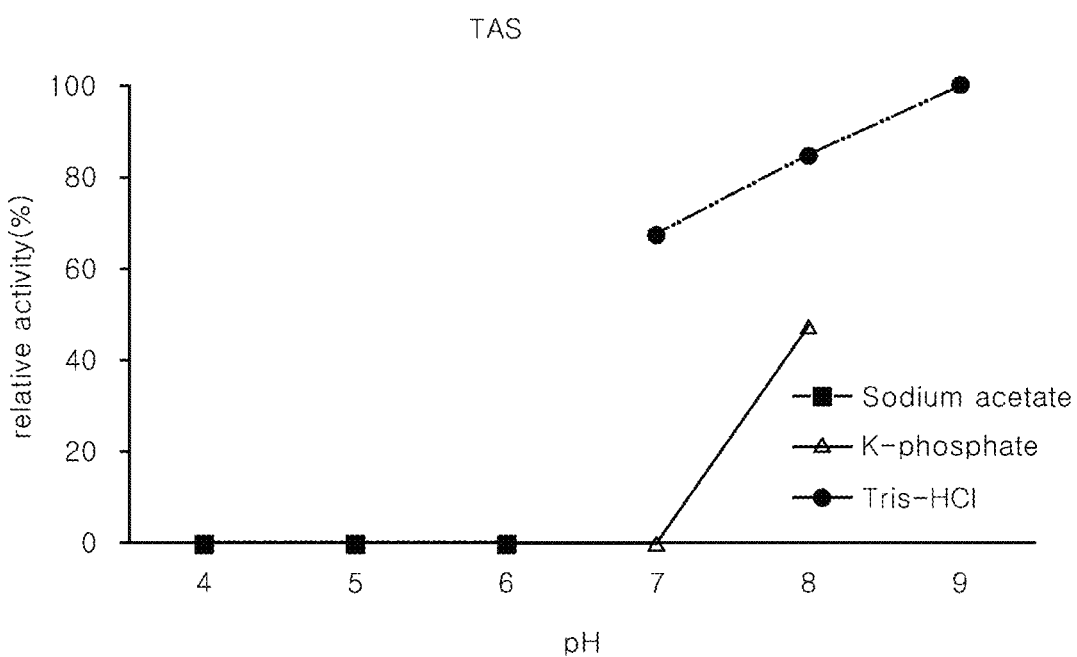
Figure 4D:
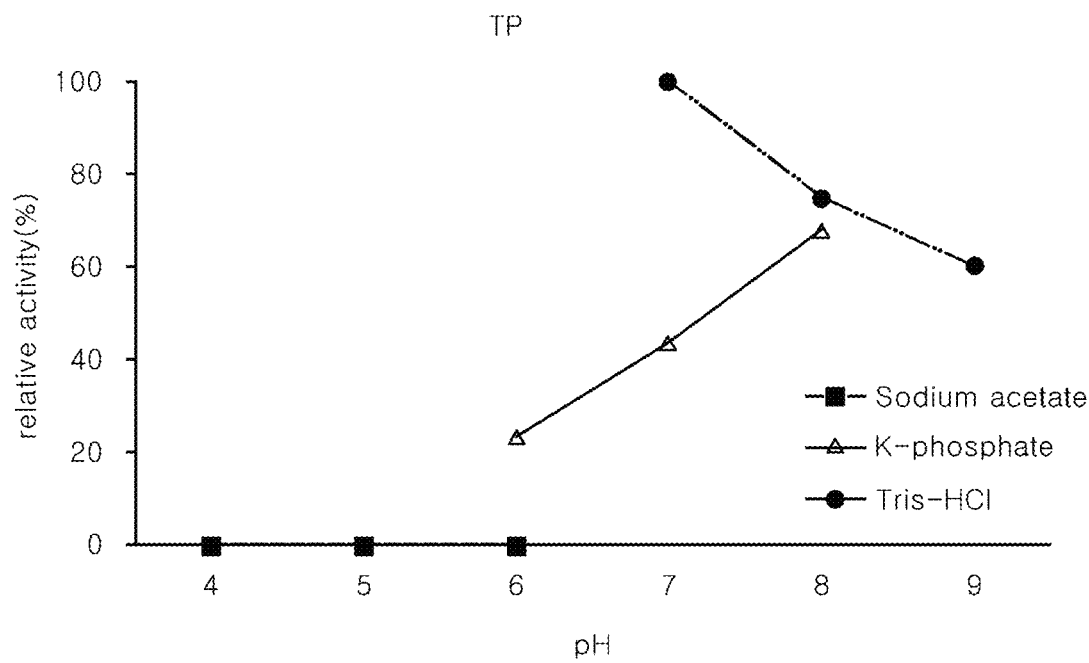
Figure 4E:
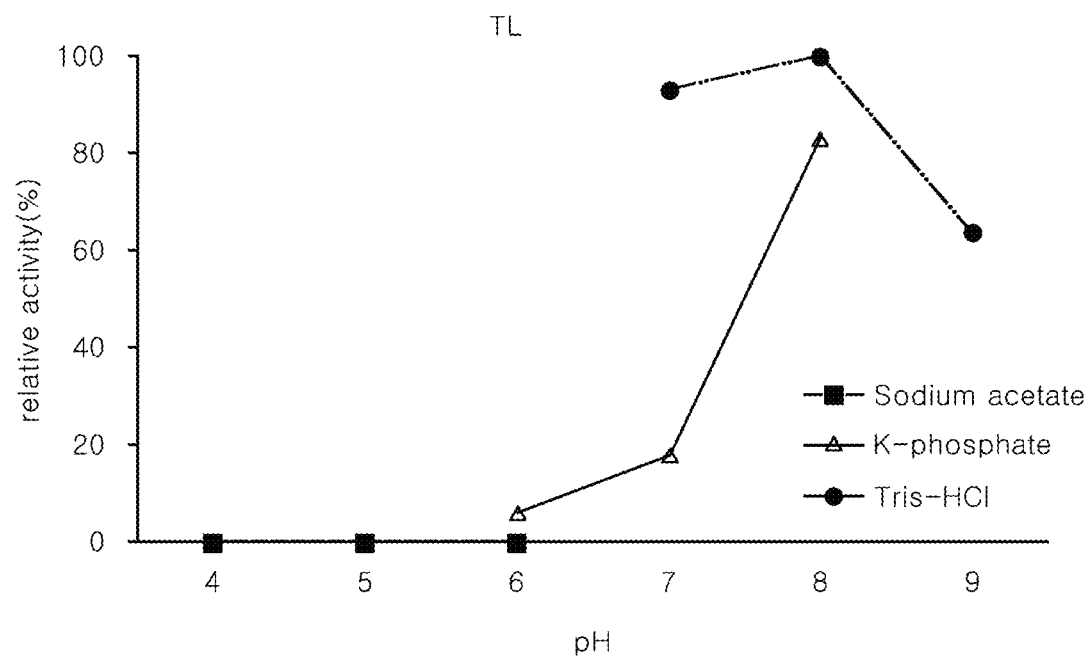
Figure 4F:
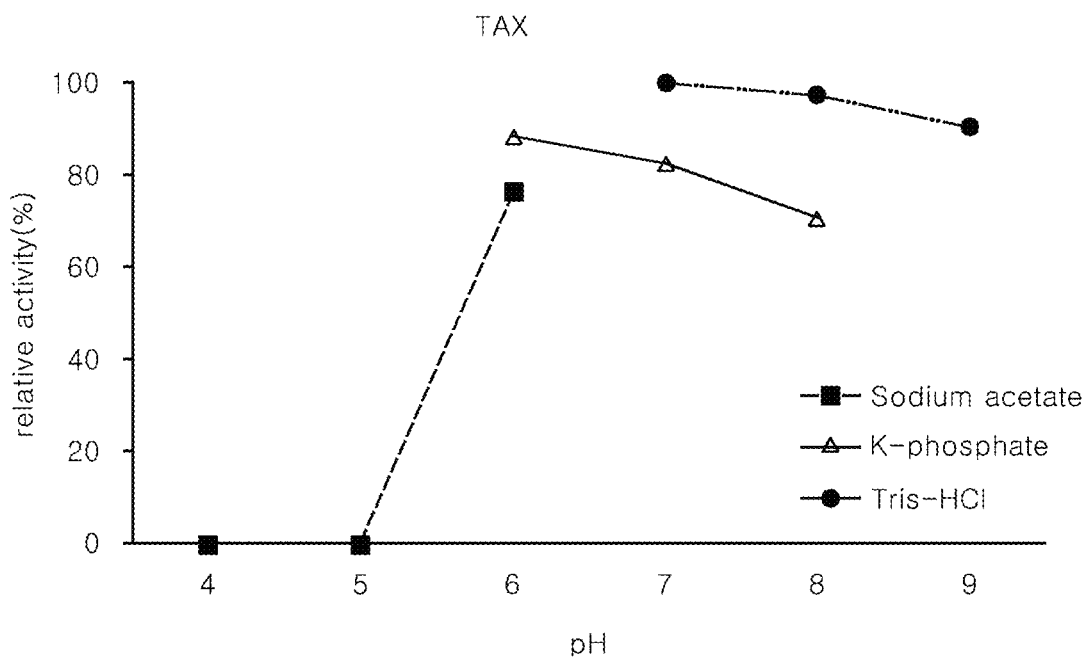
Figure 4G:
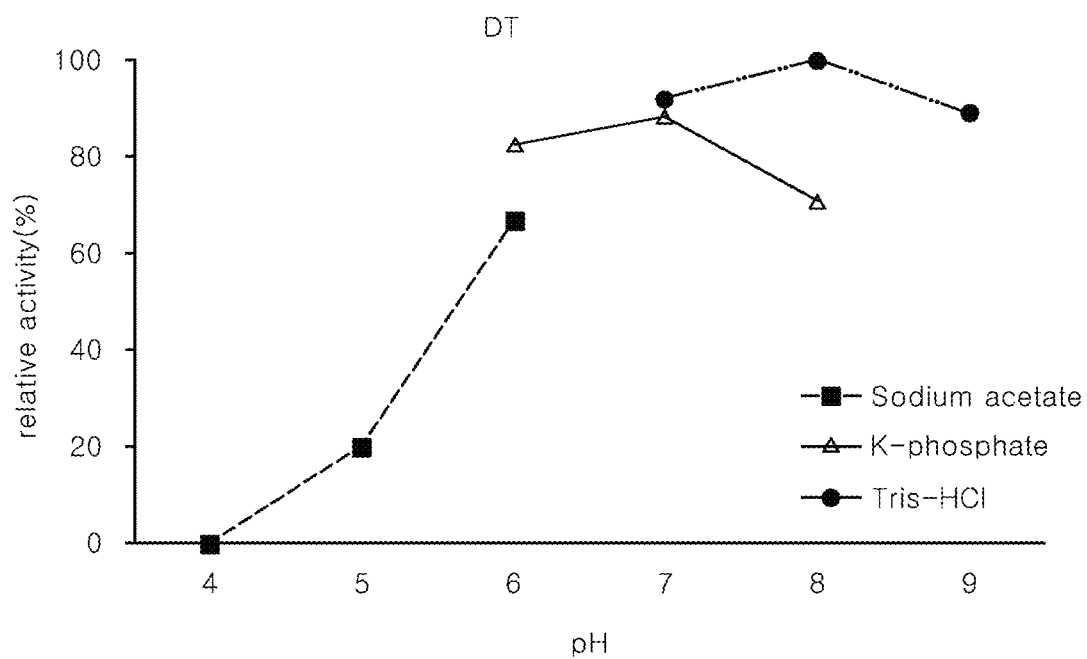

Specifically, TAX exhibited high activity at pH 7, TP, TL, RM, and DT exhibited high activity at pH8, and TAS and TAM exhibited high activity at pH 9. Further, among buffer solutions corresponding to the above pH values, it was confirmed that the Tris-HCl buffer solution exhibited the maximum activity (FIG. 4a to FIG. 4g).

Figure 5A:
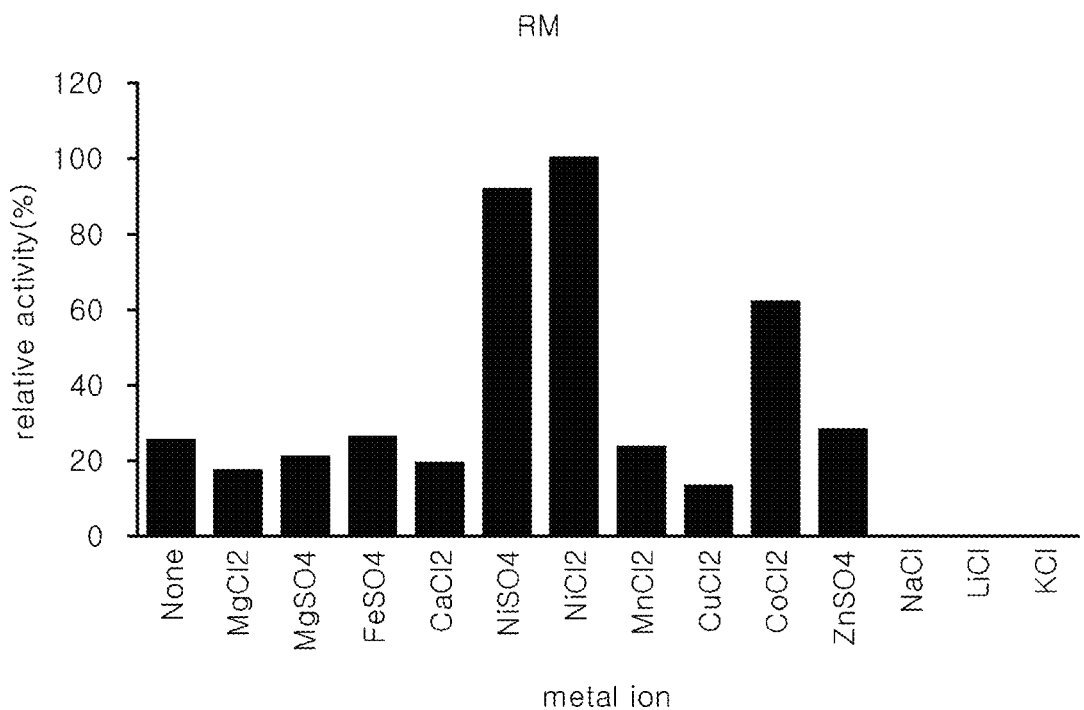
Figure 5B:
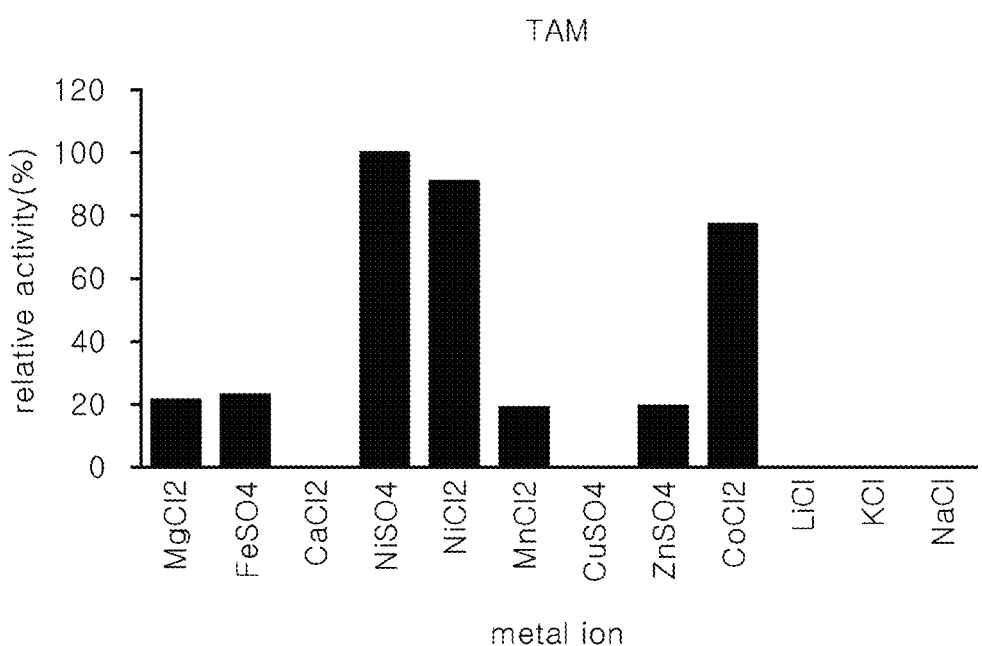
Figure 5C:
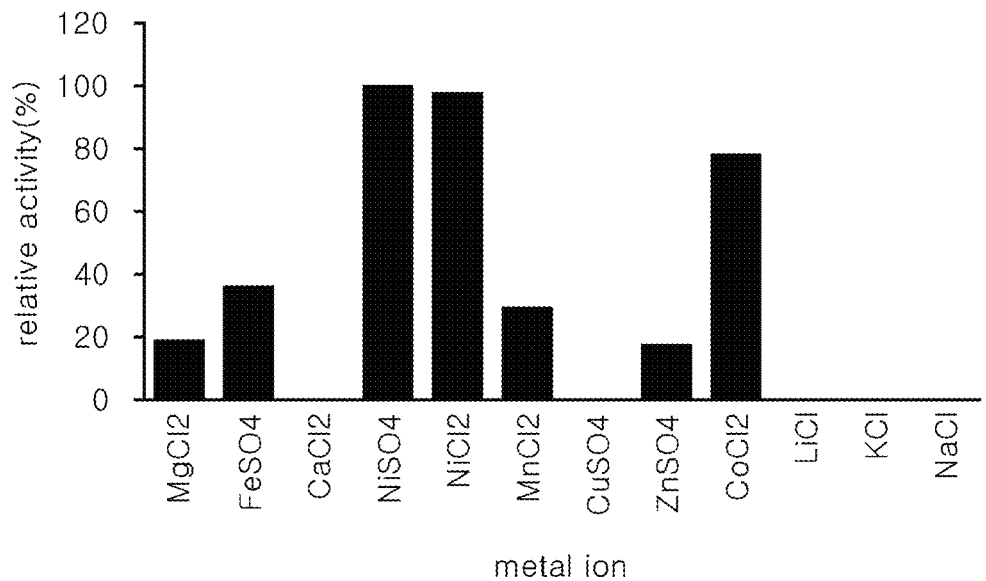
Figure 5D:
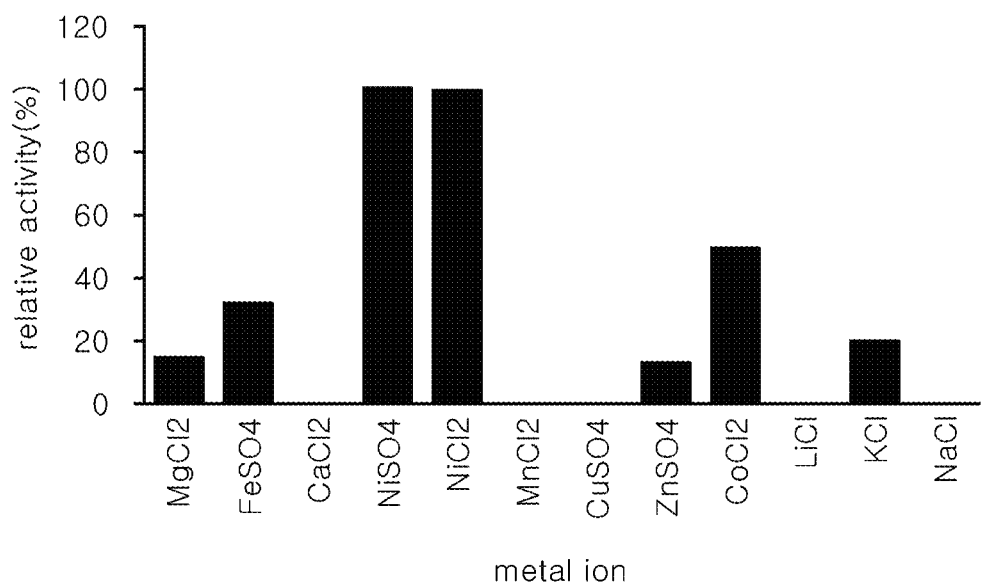
Figure 5E:
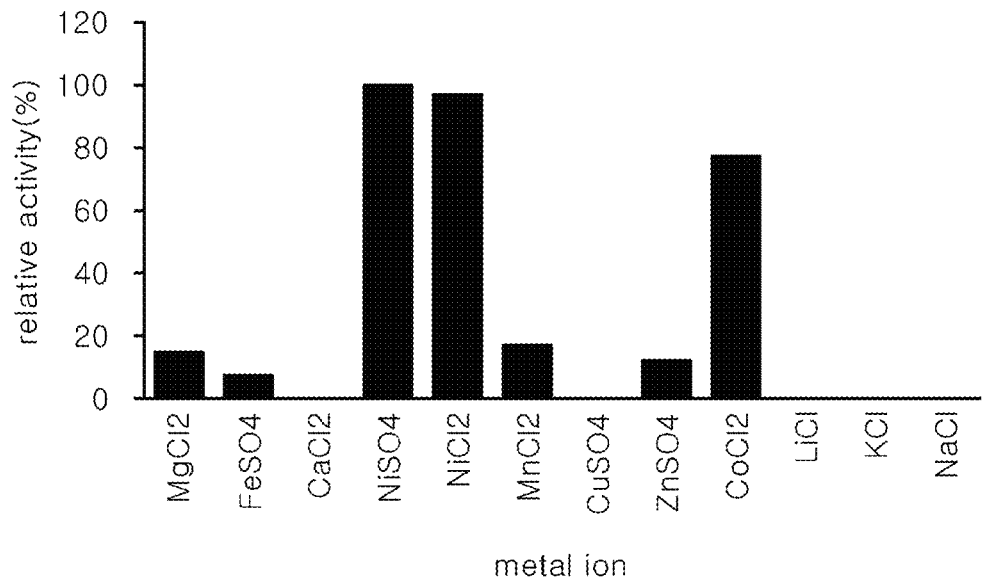
Figure 5F:
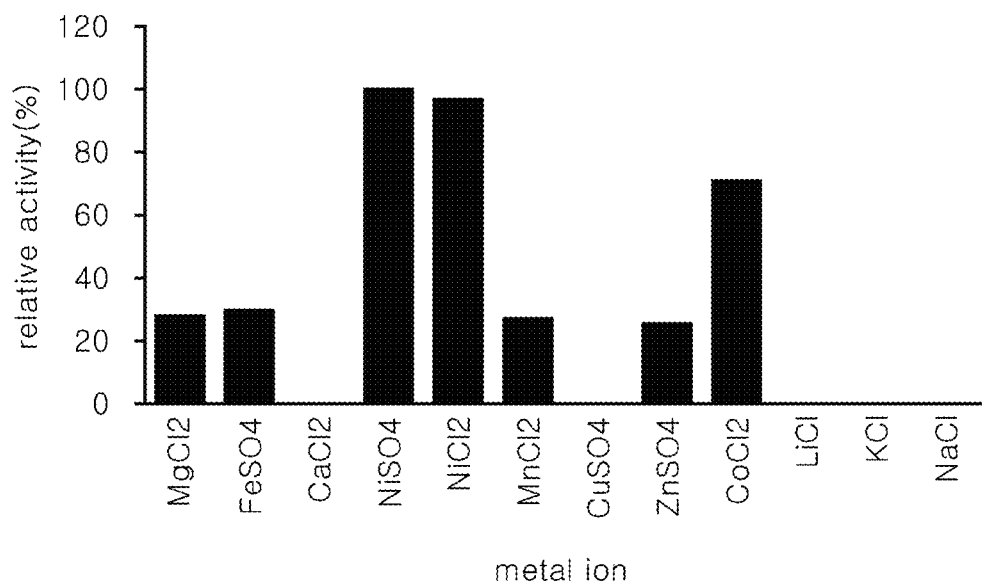

As seen from FIG. 5a to FIG. 5g, it was confirmed that enzymes of Example 2-1 could produce tagatose from fructose.

2-3. Analysis of Metal Ion Demand of D-Fructose 4-Epimerase

Previously known epimerases (psicose 3-epimerase) and isomerases (glucose isomerase, arabionose isomerase) are known to require metal ions. Evaluation was performed to determine whether metal ions have an influence on D-fructose 4-epimerases obtained in Example 2-1.

Seven proteins purified in Example 2-1 were treated with metal ions through 1 mM of NiSO$_4$, NiCl$_2$, CuCl$_2$, MnCl$_2$, CaCl$_2$, ZnSO$_4$, MgSO$_4$, MgCl$_2$, FeSO$_4$, NaCl, LiCl, KCl or CoCl$_2$, thereby measuring enzyme activity. As a control group, seven enzymes were not treated with metal ions.

Enzyme activity comparison between metal ion treated enzymes with non-treated enzymes is shown in FIG. 5a to FIG. 5g.

As shown in FIG. 5a to FIG. 5g, it was confirmed that enzymes of Example 2-1 exhibited increased activity due to addition of nickel ions and cobalt ions, which indicate requirement for metal ion. Specifically, it was confirmed that NiSO$_4$ provided maximum activity.

Example 3. Preparation of Tagatose from Fructose

Tagatose productivity was measured under optimum enzyme reaction conditions selected in Example 2. Specifically, 1 mg/ml of D-fructose 4-epimerases purified in Example 2-1 was reacted with 20 g/L (in a concentration of about 110 mM) of fructose at a reaction temperature, for example, at 80° C. for two enzymes TAM and TP, at 70° C. for five enzymes RM, TAS, TAX, TL and DT under 0.1 mM nickel sulfate, and at pH 7 for TAX, pH 8 for TP, TL, RM and DT, and at pH 9 for TAS and TAM, using a 50 mM Tris-HCl buffer solution prepared corresponding to each of the pH values.

Figure 2A:
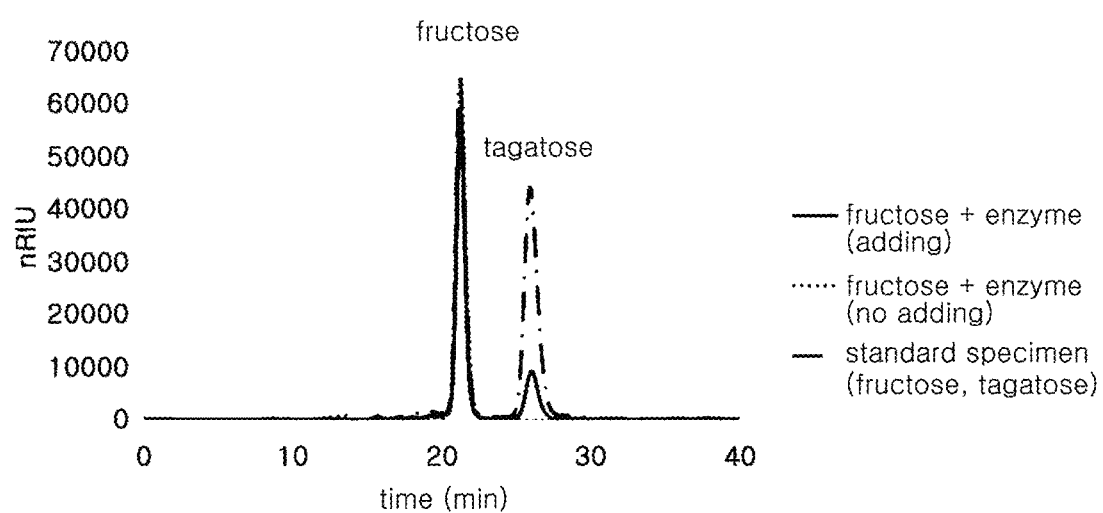
FIG. 2a to FIG. 2g show HPLC graphs depicting seven routes of preparing tagatose derived from each of thermophilic microorganisms via D-fructose 4-epimerase reactions using fructose as a substrate.
Figure 2B:
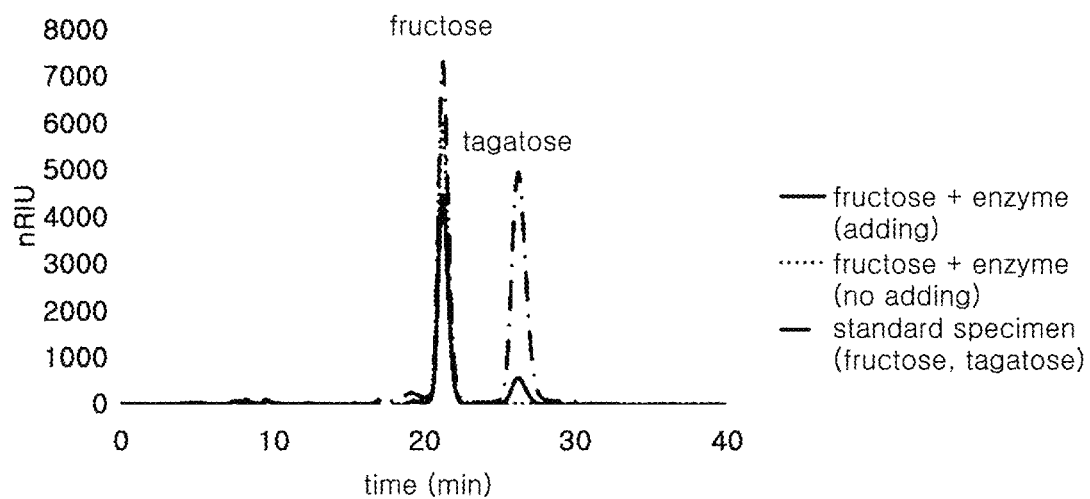
Figure 2C:
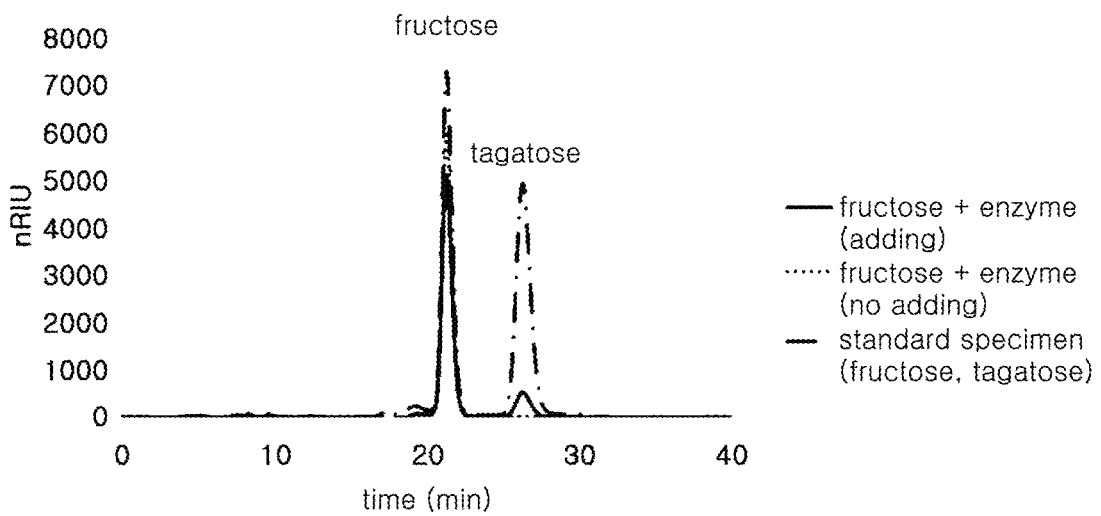
Figure 2D:
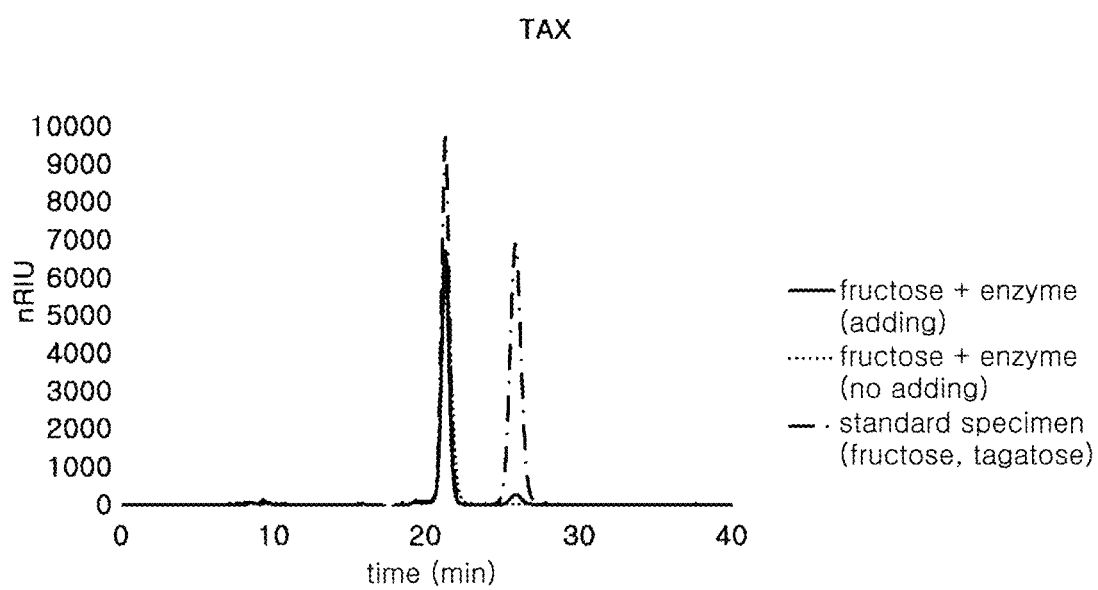
Figure 2E:
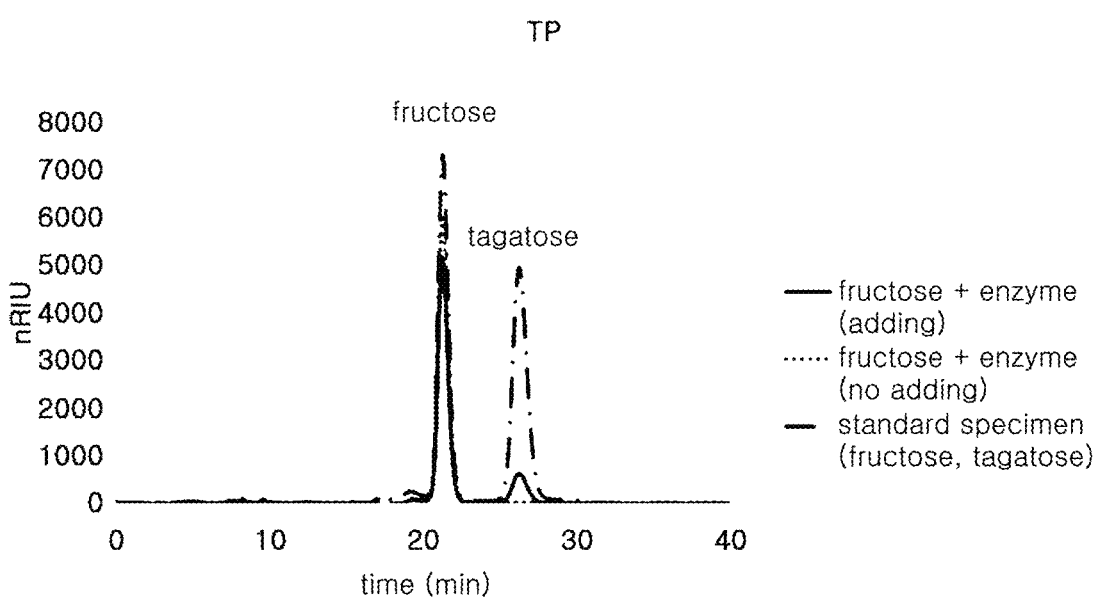
Figure 2F:
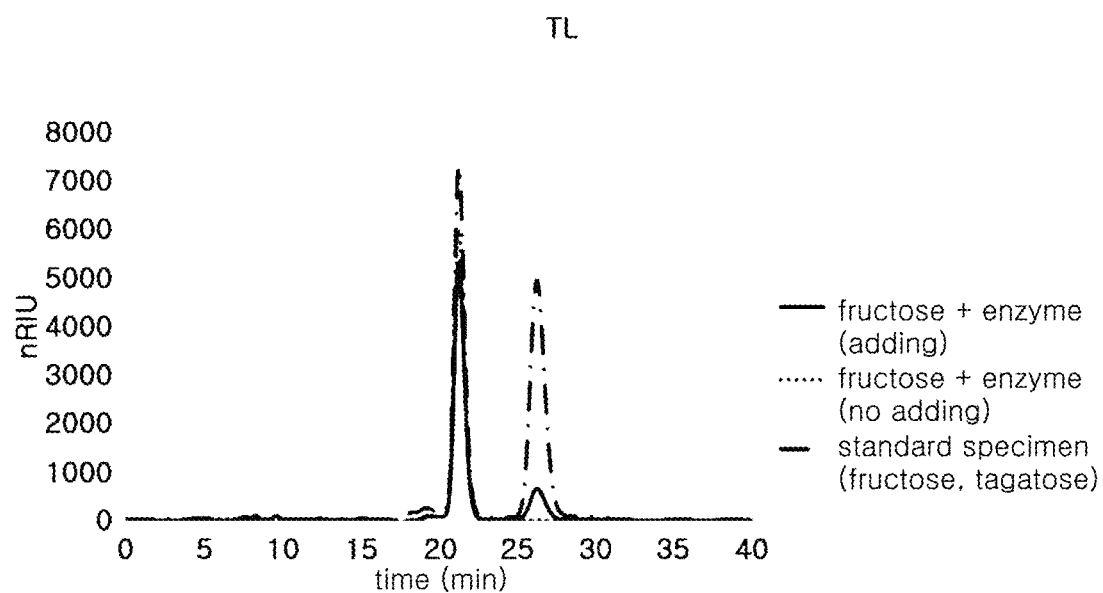
Figure 2G:
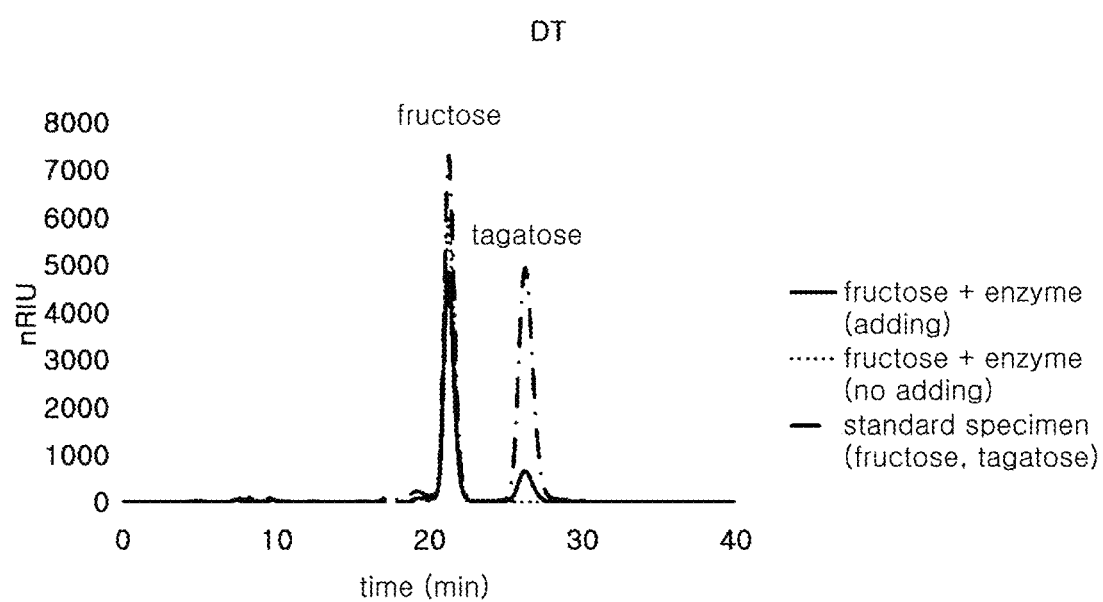

HPLC analysis was performed by the same method as in Example 2-2 (FIG. 2a to FIG. 2g). Conversion rate from fructose to tagatose was determined from tagatose amount produced from the reaction. Results are shown in Table 2.

TABLE 2

|  | Fructose concentration (g/L) | Tagatose concentration (g/L) | Conversion rate (%) |
| --- | --- | --- | --- |
| RM | 20 | 3.8 | 19.0 |
| TAX | 20 | 1.7 | 8.6 |
| TAM | 20 | 3.3 | 16.7 |
| TAS | 20 | 2.5 | 12.4 |
| TP | 20 | 3.6 | 18.1 |
| TL | 20 | 3.9 | 19.4 |
| DT | 20 | 2.5 | 12.6 |

The solution after above reaction (a mixed solution of tagatose and fructose) was subjected to decolorization (using activated carbon), ion exchange purification, chromatography, and crystallization processes, thereby harvesting final crystalline tagatose.

The invention claimed is:

1. A method of producing tagatose, the method comprising:
contacting fructose with a protein or a microorganism expressing the protein comprising an amino acid sequence selected from the group consisting of SEQ ID NOs: 1 to 7 such that the fructose is enzymatically converted to tagatose.

2. The method of producing tagatose according to claim 1, wherein contacting is performed under at least one of the following conditions:
at a temperature between 50° C. and 90° C.,
at a pH between 6.0 and 10.0, and
at a fructose concentration of 5% (w/v) to 60% (w/v).

3. The method according to claim 2, wherein the protein has amino acid sequence of SEQ ID NO: 7, wherein contacting is performed at a temperature between 50° and 80° C.

4. The method according to claim 2, wherein the protein has an amino acid sequence of SEQ ID NO: 1, 3, 5, 6 or 7, wherein contacting is performed at a temperature between 60° C. and 80° C.

5. The method according to claim 2, wherein the protein has an amino acid sequence of SEQ ID NO: 2 or 4, wherein contacting is performed at a temperature between 70° C. and 90° C.

6. The method according to claim 2, wherein the protein has an amino acid sequence of SEQ ID NO: 1 or 6, wherein contacting is performed at a pH between 6.0 and 9.0.

7. The method according to claim 2, wherein the protein has an amino acid sequence of SEQ ID NO: 4 or 7, wherein contacting is performed at a pH between 7.0 and 10.0.

8. The method according to claim 2, wherein the protein has an amino acid sequence of SEQ ID NO: 1, 2, 3, or 5, wherein contacting is performed at a pH between 7.0 and 9.0.

9. The method according to claim 2, wherein the protein has an amino acid sequence of SEQ ID NO: 4 or 7, wherein contacting is performed at a pH between 8.0 and 10.0.

10. The method according to claim 2, wherein the protein has an amino acid sequence of SEQ ID NO: 6, wherein contacting is performed at a pH between 6.0 and 8.0.

11. The method of producing tagatose according to claim 1, further comprising adding magnesium ions, zinc ions, nickel ions, cobalt ions, iron ions, manganese ions or a mixture of two or more of the foregoing.

12. The method according to claim 1, further comprising converting fructose into tagatose through epimerization at carbon-4 position of fructose.

13. The method according to claim 1, wherein in place of the protein to be used in the contacting step, a microorganism expressing protein having an amino acid sequence set forth in any one of SEQ ID NOs: 1 to 7 is used.

14. The method according to claim 1, wherein the protein having an amino acid sequence set forth in SEQ ID NO: 1 is derived from *Rhodothermus marinus*.

15. The method according to claim 1, wherein the protein having an amino acid sequence set forth in SEQ ID NO: 2 is derived from *Thermotoga petrophila*.

16. The method according to claim 1, wherein the protein having an amino acid sequence set forth in SEQ ID NO: 3 is derived from *Thermotoga lettingae*.

17. The method according to claim 1, wherein the protein having an amino acid sequence set forth in SEQ ID NO: 4 is derived from *Thermoanaerobacter mathranii*.

18. The method according to claim 1, wherein the protein having an amino acid sequence set forth in SEQ ID NO: 5 is derived from *Dictyoglomus turgidum*.

19. The method according to claim 1, wherein the protein having an amino acid sequence set forth in SEQ ID NO: 6 is derived from *Thermoanaerobacterium xylanolyticum*.

20. The method according to claim 1, wherein the protein having an amino acid sequence set forth in SEQ ID NO: 7 is derived from *Thermoanaerobacter siderophilus*.

* * * * *